United States Patent
Akiyama et al.

(10) Patent No.: US 7,705,196 B2
(45) Date of Patent: Apr. 27, 2010

(54) SFRP EXPRESSION ENHANCING AGENT

(75) Inventors: Tetsu Akiyama, Tama (JP); Takefumi Ishidao, Tokyo (JP); Tomoiki Aiba, Arai (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 530 days.

(21) Appl. No.: 10/594,695

(22) PCT Filed: Mar. 30, 2005

(86) PCT No.: PCT/JP2005/006163

§ 371 (c)(1),
(2), (4) Date: Jan. 10, 2007

(87) PCT Pub. No.: WO2005/094887

PCT Pub. Date: Oct. 13, 2005

(65) Prior Publication Data

US 2008/0227695 A1    Sep. 18, 2008

(30) Foreign Application Priority Data

Mar. 31, 2004    (JP) .............................. 2004-106315

(51) Int. Cl.
    G01N 33/00    (2006.01)
    C12Q 1/00    (2006.01)
(52) U.S. Cl. ............................. 800/3; 424/4
(58) Field of Classification Search ........................ None
    See application file for complete search history.

(56) References Cited

OTHER PUBLICATIONS

Moreadith et al., J. Mol. Med. 1997;75(3):208-16.*
Mullins et al. Journal of Clinical Investigation, 1996;97:1557-60.*
Denning et al. Nat Biotech 2001;19:559-562.*
Yanagimachi, Mol Cell Endocrinol 2002;187:241-8.*
Wilmut, Cloning Stem Cell 2003;5:99-100.*
Polejaeva et al. Nature 2000;407:86.*
Levanon, EMBO Reports 2003;4:560-4.*
Hanada et al., "NE-dlg, A Mammalian Homolog of *Drosophila* DLG Tumor Suppressor, Induces Growth Suppression and Impairment of Cell Adhesion: Possible Involvement of Down-Regulation of β-Catenin by NE-dlg Expression," Int. J. Cancer, No. 86, 2000, pp. 480-488.
Akiyama, "APC Function and Cancer," Journal of Clinical and Experimental Medicine, vol. 182, No. 1, 1997, pp. 103-107 (with English translation attached).
Elder et al., "cDNA Sequence and Genomic Structure of the Murine p55 (Mpp1) Gene," Genomics, 38, Article No. 0621, 1996, pp. 231-234.
Matsumine et al., "Binding of APC to the Human Homolog of the *Drosophila* Discs Large Tumor Suppressor Protein," Science, vol. 272, May 17, 1996, pp. 1020-1023.
Willert et al., "Wnt proteins are lipid-modified and can act as stem cell growth factors," Nature, vol. 423, May 22, 2003, pp. 448-452.
Reya et al., "A role for Wnt signalling in self-renewal of haematopoietic stem cells," Nature, vol. 423, May 22, 2003, pp. 409-414.
Kawano et al., "Secreted antagonists of the Wnt signalling pathway," Journal of Cell Science, No. 116, 2003, pp. 2627-2634.
Jones et al., "Secreted: Frizzled-related proteins: searching for relationships and patterns," BioEssays, No. 24, 2002, pp. 811-820.
Suzuki et al., "Epigenetic inactivation of SFRP genes allows constitutive WNT signaling in colorectal cancer," Nature Genetics, vol. 36, No. 4, Apr. 2004, pp. 417-422.
Xu et al., "Functional and biochemical interactions of Wnts with FrzA, a secreted Wnt antagonist," Development, No. 125, 1998, pp. 4767-4776.
Chang et al., "Cloning and characterization of a secreted frizzled-related protein that is expressed by the retinal pigment epithelium," Human Molecular Genetics, vol. 8, No. 4, 1999, pp. 575-583.
Supplementary European Search Report issued in corresponding European Patent Application No. EP 05 72 7369 dated Jun. 5, 2009 (6 pages).
Ishidate et al., "The APC-hDLG complex negatively regulates cell cycle progression from the G0/G1 to S phase," Oncogene, vol. 19, No. 3, Jan. 20, 2000, pp. 365-372 (8 pages).
Suzuki et al., "Tax oncoprotein of HTLV-1 binds to the human homologue of *Drosophila* discs large tumor suppressor protein, hDLG, and perturbs its function in cell growth control," Oncogene, vol. 18, No. 44, Oct. 28, 1999, pp. 5967-5972 (6 pages).
Hough et al., "Organizing a functional junctional complex requires specific domains of the *Drosophilia* MAGUK Discs large," Genes & Development, vol. 11, No. 23, Dec. 1, 1997, pp. 3242-3253 (12 pages).
Woods et al., "The Discs-Large Tumor Suppressor Gene of *Drosophila* Encodes a Guanylate Kinase Homolog Localized at Septate Junctions," Cell, vol. 66, No. 3, Aug. 9, 1991, pp. 451-464 (14 pages).

* cited by examiner

*Primary Examiner*—Q. Janice Li
(74) *Attorney, Agent, or Firm*—Kilyk & Bowersox, P.L.L.C.

(57) ABSTRACT

Tumor formation and reduced transcription of both sFRP1 gene and sFRP2 gene were found in Dlg gene knock-out mice, and thereby the following has been provided: an agent for enhancing the expression and/or function of sFRP, containing a compound having an effect of enhancing the expression and/or function of Dlg; an agent for inhibiting tumor formation or an agent for preventing and/or treating a tumor disease, containing the agent for enhancing the expression and/or function of sFRP; a method of enhancing the expression and/or function of sFRP, comprising enhancing the expression and/or function of Dlg; a method of inhibiting tumor formation or a method of preventing and/or treating a tumor disease, comprising using the aforementioned enhancing agent or the aforementioned enhancing method; a non-human mammal that is deficient in one or both of Dlg alleles; a cell originating in the mammal; a method of identifying a compound, comprising using the mammal or the cell; and a method of examining a tumor tissue or a tumor cell, comprising measuring the expression and/or function of Dlg.

8 Claims, 4 Drawing Sheets

Figure 1-A
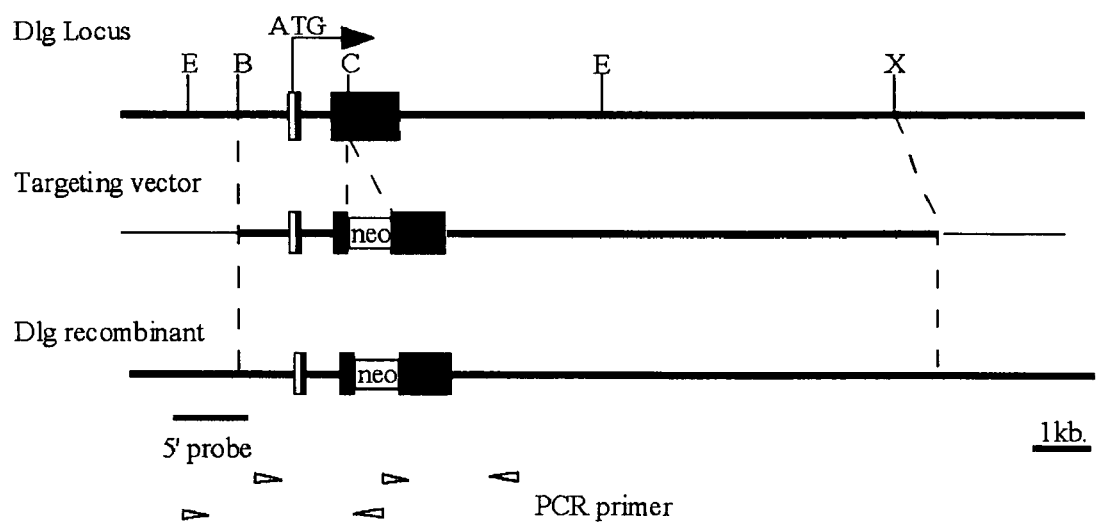
Figure 1-B
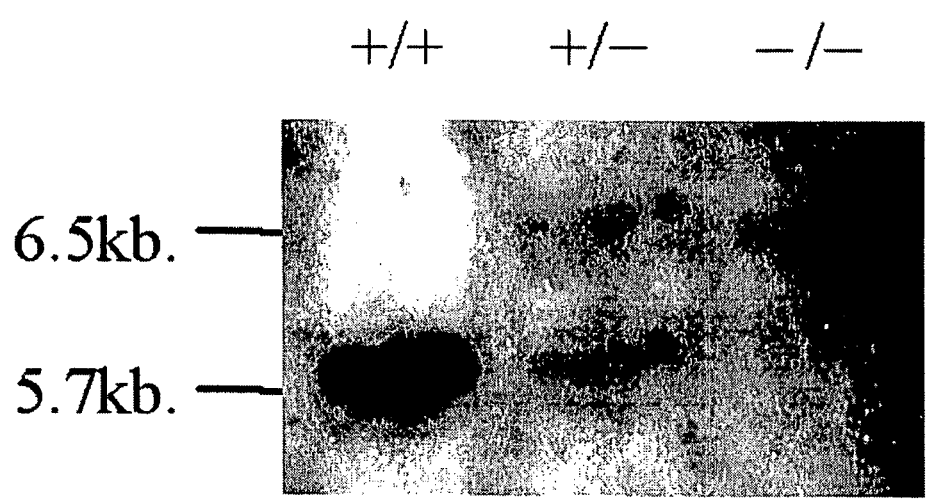

Figure 1-C
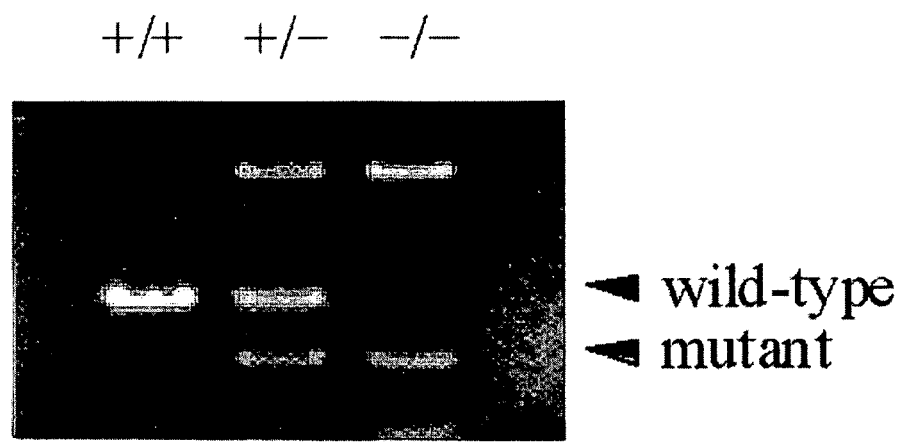
Figure 1-D
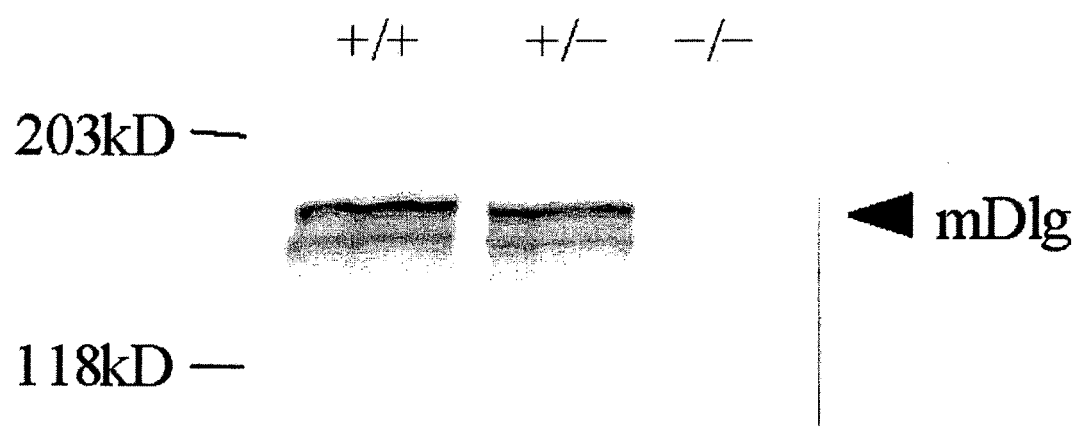

Figure 2-A
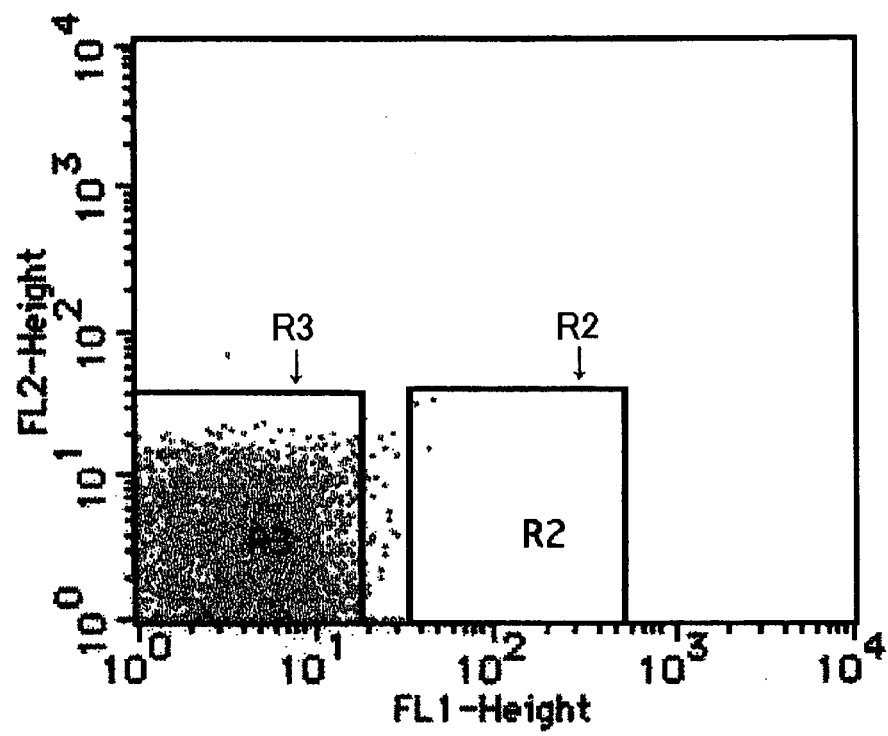
Figure 2-B
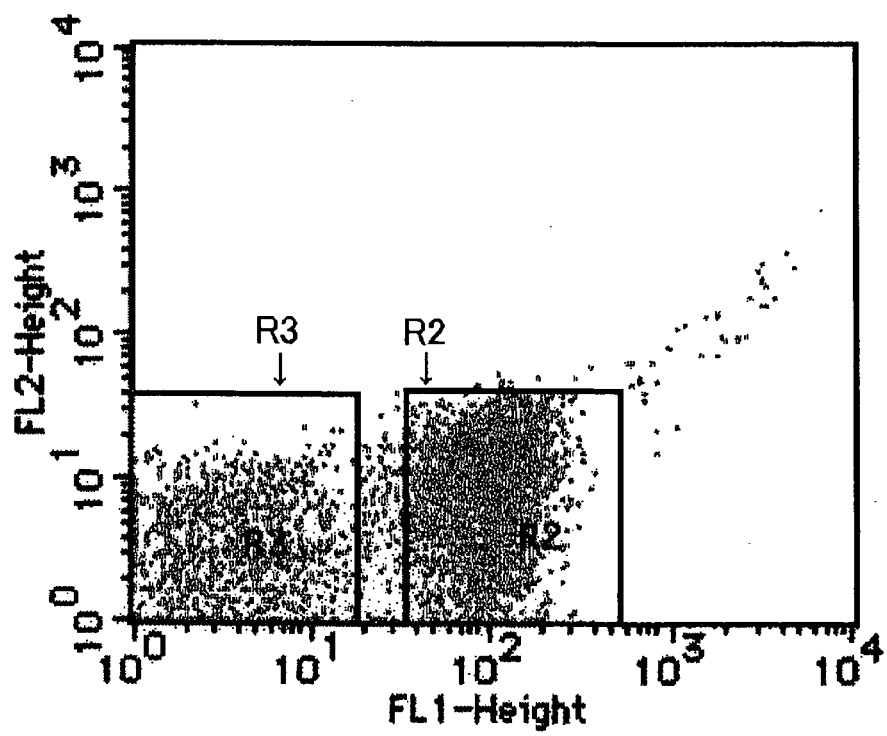

Figure 3
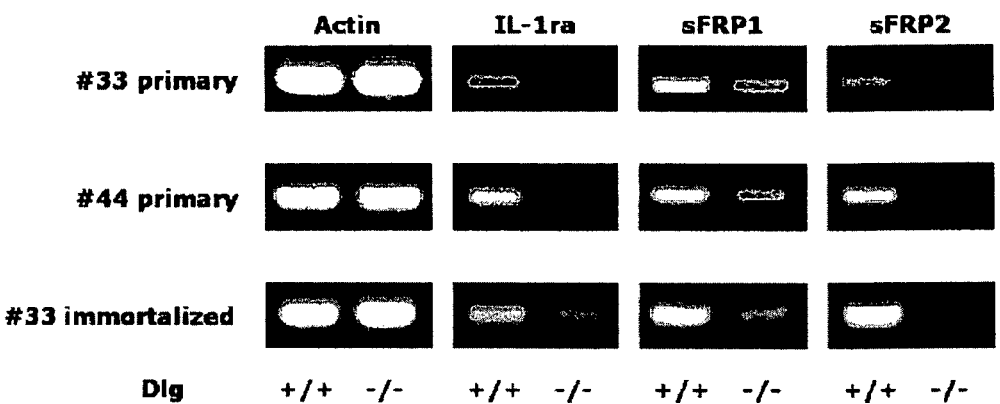
Figure 4
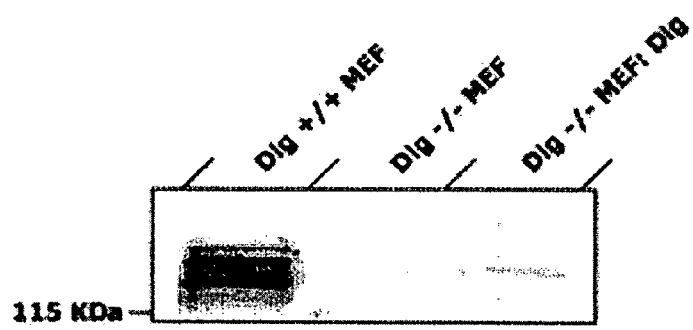
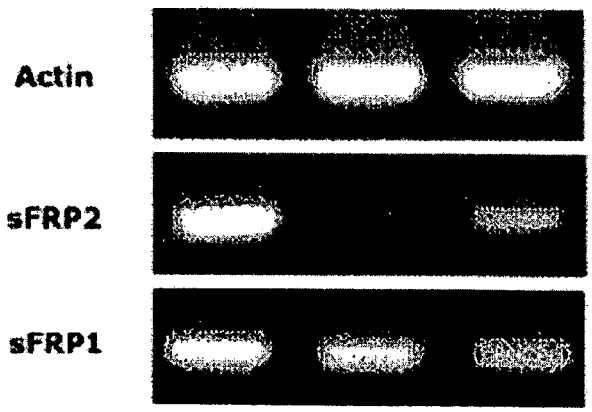

SFRP EXPRESSION ENHANCING AGENT

This application is a National Stage Application of PCT/JP2005/006163, filed Mar. 30, 2005.

TECHNICAL FIELD

The present invention relates to an agent for enhancing the expression and/or function of sFRP (secreted frizzled-related protein), containing a compound having an effect of enhancing the expression and/or function of Dlg (discs large). Further, the present invention relates to an agent for inhibiting tumor formation, containing the agent for enhancing the expression and/or function of sFRP. Furthermore, the present invention relates to an agent for preventing and/or treating a tumor disease, containing the agent for enhancing the expression and/or function of sFRP. Further, the present invention relates to a method of enhancing the expression and/or function of sFRP, comprising enhancing the expression and/or function of Dlg. Furthermore, the present invention relates to a method of inhibiting tumor formation, comprising using the agent for enhancing the expression and/or function of sFRP, or using the method of enhancing the expression and/or function of sFRP. Further, the present invention relates to a method of preventing and/or treating a tumor disease, comprising using the agent for enhancing the expression and/or function of sFRP, or using the method of enhancing the expression and/or function of sFRP. Furthermore, the present invention relates to a method of identifying a compound, comprising using a non-human mammal which is deficient in one of Dlg alleles. Further, the present invention relates to a method of identifying a compound, comprising using a cell originating in a non-human mammal which is deficient in one or both of Dlg alleles. Furthermore, the present invention relates to a non-human mammal which is deficient in one or both of Dlg alleles, and to a cell originating in the non-human mammal. Further, the present invention relates to a method of examining a tumor tissue or a tumor cell, comprising measuring the expression and/or function of Dlg gene and/or Dlg.

BACKGROUND OF INVENTION

Dlg gene is found to be expressed ubiquitously in many tissues and cells. Dlg gene encodes a protein (hereinafter, may be referred to Dlg) which is reported to bind to APC (adenomatous polyposis coli) via the C-terminal XVT motif of APC (Non-Patent Reference 1). APC gene was isolated as a responsible gene for familial adenomatous polyposis (hereinafter, may be referred to FAP). An abnormal APC gene has been detected in FAP and also in many cases of sporadic colorectal tumor. This suggests that the abnormal APC gene may be an important factor for onset of colorectal cancer. In addition, over-expression of APC blocks cell cycle progression. The expression of both Dlg and APC was found in rat colon epithelial cells and at the synapse in cultured hippocampal neurons. These findings suggest that the Dlg-APC complex may participate in regulation of both cell cycle progression and neuronal function.

APC gene encodes a large protein of 300 kDa (hereinafter, may be referred to APC) which forms a complex with β-catenin and negatively regulates Wnt/Wingless signal (hereinafter, may be referred to Wnt signal) transduction pathway. The Wnt signal was found as a signal transduction system involved in regulation of morphogenesis, and is known to participate in numerous events including development, regulation of stem cell differentiation, and tumor formation. Recently, the Wnt signal was reported to be an important factor for stem cell in its proliferation regulation and survival (Non-Patent References 2 and 3).

The Wnt signal induced by Wnt ligand is transduced into a cell via a frizzled membrane receptor (hereinafter, may be referred to Fz) on the cell membrane.

In recent years, a secretory protein that binds to both Fz and Wnt, namely sFRP, was found out (Non-Patent Reference 4). sFRP binds to Fz and Wnt outside a cell and works as an antagonist of the Wnt signal, and thereby participates in regulation of the Wnt signal (Non-Patent Reference 5). In addition, it was reported that the sFRP function was reduced in a colorectal cancer cell due to methylation of sFRP gene and that restoration of the sFRP function in a colorectal cancer cell induced reduction of the Wnt signal in the cell (Non-Patent Reference 6).

Non-patent Reference 1: Matsumine, A. et al., Science, 1996, Vol. 272, p. 1020-1023.

Non-patent Reference 2: Willert, K. et al., Nature, 2003, Vol. 423, p. 448-452.

Non-patent Reference 3: Reya, T. et al., Nature, 2003, Vol. 423, p. 409-414.

Non-patent Reference 4: Kawano, Y. et al., Journal of Cell Science, 2003, Vol. 116, p. 2627-2634.

Non-patent Reference 5: Jones, S. E. et al., BioEssays, 2002, Vol. 24, p. 811-820.

Non-patent Reference 6: Suzuki, H. et al., Nature Genetics, 2004, Vol. 36, p. 417-422 (published online on Mar. 14, 2004).

DISCLOSURE OF THE INVENTION

Problem to be Solved by the Invention

Dlg gene is considered to be a tumor suppressor gene in view of the report showing that Dlg gene deficiency in *drosophila* resulted in neuroblastoma formation. Further, Dlg is considered to relate to the Wnt signal, since Dlg binds to APC that participates in regulation of the Wnt signal involved in tumor formation. However, there are no reports that show Dlg gene acting as a tumor suppressor gene in a mammal. In addition, there are no reports demonstrating the relation of Dlg to the Wnt signal.

Elucidation of the effect of Dlg in a mammal and of its effect mechanism allows regulation of the expression and/or function of Dlg, and thereby allows development of the means for preventing or treating an abnormal living body function or a disease which is due to Dlg gene, Dlg, and the abnormality thereof in expression or function.

The object of the present invention is to provide a means for recovering an abnormal living body function due to Dlg gene, Dlg, and the abnormality thereof in expression or function, by regulating the expression and/or function of Dlg. In addition, the object of the present invention is to provide a means for preventing or treating a disease due to Dlg gene, Dlg, and the abnormality thereof in expression or function.

Means for Solving the Object

The present inventors have concentrated their efforts to meet the aforementioned object and have generated Dlg gene knock-out mice by means of genetic engineering techniques. Further, the present inventors found tumor formation in Dlg gene heterozygous deficient mice and a significant association of Dlg gene deficiency with the tumor formation. Furthermore, the present inventors have found that Dlg gene deficiency induced reduction in transcription products of both sFRP1 gene and sFRP2 gene. The present invention has been thus achieved.

In various embodiments, the present invention relates to an agent for enhancing the expression and/or function of sFRP, containing a compound having an effect of enhancing the expression and/or function of Dlg.

The present invention also relates to an agent for enhancing the expression and/or function of sFRP, containing at least one member selected from Dlg, Dlg gene and a recombinant vector containing Dlg gene.

The present invention further relates to the aforementioned agent for enhancing the expression and/or function of sFRP, wherein sFRP is sFRP2.

The present invention still further relates to an agent for inhibiting tumor formation, containing the aforementioned agent for enhancing the expression and/or function of sFRP.

The present invention also relates to an agent for preventing and/or treating a tumor disease, containing the aforementioned agent for enhancing the expression and/or function of sFRP.

The present invention further relates to a method of enhancing the expression and/or function of sFRP, comprising enhancing the expression and/or function of Dlg.

The present invention still further relates to the aforementioned method of enhancing the expression and/or function of sFRP, comprising using at least one member selected from Dlg, Dlg gene and a recombinant vector containing Dlg gene.

The present invention also relates to the aforementioned method of enhancing the expression and/or function of sFRP, wherein sFRP is sFRP2.

The present invention further relates to a method of inhibiting tumor formation, comprising using the aforementioned agent for enhancing the expression and/or function of sFRP.

The present invention still further relates to a method of inhibiting tumor formation, comprising using the aforementioned method of enhancing the expression and/or function of sFRP.

The present invention also relates to a method of preventing and/or treating a tumor disease, comprising using the aforementioned agent for enhancing the expression and/or function of sFRP.

The present invention further relates to a method of preventing and/or treating a tumor disease, comprising using the aforementioned method of enhancing the expression and/or function of sFRP.

The present invention still further relates to a method of identifying a compound, comprising using a non-human mammal that is deficient in one of Dlg alleles, wherein the compound is any one of the following:
(i) a compound having an effect of enhancing the expression and/or function of Dlg;
(ii) a compound having an effect of enhancing the expression and/or function of sFRP; and
(iii) a compound that inhibits tumor formation.

The present invention also relates to a method of identifying a compound, comprising using a cell originating in a non-human mammal that is deficient in one or both of Dlg alleles, wherein the compound is any one of the following:
(i) a compound having an effect of enhancing the expression and/or function of Dlg;
(ii) a compound having an effect of enhancing the expression and/or function of sFRP; and
(iii) a compound that inhibits tumor formation.

The present invention further relates to the aforementioned method of identifying a compound, wherein sFRP is sFRP2.

The present invention still further relates to a non-human mammal that is deficient in one or both of Dlg alleles.

The present invention also relates to a cell originating in a non-human mammal that is deficient in one or both of Dlg alleles.

The present invention further relates to a method of examining a tumor tissue or a tumor cell, comprising measuring the expression and/or function of Dlg in a test tissue or a test cell and detecting reduction or deletion of the expression and/or function in comparison to a normal tissue or a normal cell.

ADVANTAGE OF THE INVENTION

The present invention can provide an agent for enhancing the expression and/or function of sFRP, an agent for inhibiting tumor formation containing said enhancing agent, and an agent for preventing and/or treating a tumor disease containing said enhancing agent. Further, the present invention can provide a method of enhancing the expression and/or function of sFRP, a method of inhibiting tumor formation, and a method of preventing and/or treating a tumor disease. These agents can be used for preventing and treating a tumor disease. These agents and methods can be utilized in elucidating the mechanism of Dlg-associated expression and/or function of sFRP and for elucidating the mechanism of Dlg deficiency-associated tumor formation.

Further, the present invention can provide a Dlg deficient non-human mammal and a cell originating in said mammal, which allows execution of a method of identifying a compound having an effect of enhancing the expression and/or function of Dlg, a compound having an effect of enhancing the expression and/or function of sFRP and a compound that inhibits tumor formation. The compound obtained by the present identification method can be used for an effective ingredient for the agent for enhancing the expression and/or function of sFRP, the agent for inhibiting tumor formation, and the agent for preventing and/or treating a tumor disease. In addition, the compound can be used for conducting the method of enhancing the expression and/or function of sFRP, the method of inhibiting tumor formation and the method of preventing and/or treating a tumor disease.

Furthermore, the present invention can provide a method of examining a tumor tissue or a tumor cell, comprising measuring the expression and/or function of Dlg.

BRIEF DESCRIPTION OF THE DRAWINGS

FIG. 1-A is a diagrammatic representation of the Dlg Locus (in the figure, referred to Dlg Locus), targeting construct (in the figure, referred to targeting vector), and Dlg gene (in the figure, referred to Dlg recombinant) introduced by homologous recombination. Neomycin resistant gene (neo) was inserted into the ClaI site by in-frame fusion. The Neomycin resistant gene was flanked by 0.8-kb and 8.5-kb homologous sequence at 5, and 3' sides (shown by thick lines), respectively. The thin line indicates the sequences derived from pBluescript. The locations of 5' probe used for Southern blot analyses are given with the expected sizes of hybridizing fragment below. The marks in the figure are as follows: (B) BamHI; (C) ClaI; (E) EcoRI; and (X) XhoI. The arrow and ATG indicates the start site of Dlg coding region. (Example 1)

FIG. 1-B shows a representative Southern blot of tail DNA from Dlg +/+ mouse, Dlg +/− mouse, and Dlg −/− mouse of the third filial generation detected by 5' probe. (Example 1)

FIG. 1-C shows the result of genotype analysis of Dlg +/+ mouse, Dlg +/− mouse, and Dlg −/− mouse of the third filial generation, using tail DNA from each mouse. In the figure, "wild-type" indicates wild type Dlg gene, while "mutant" indicates mutated Dlg gene. (Example 1)

FIG. 1-D shows the result of Dlg expression analysis in Dlg +/+ mouse, Dlg +/− mouse, and Dlg −/− mouse of the third filial generation, using brain lysates of newborn mice. (Example 1)

FIG. 2-A shows the result of flow-cytometer analysis of the lymph node of Dlg +/+ mouse, indicating that the lymph node contains almost no cells stained with a FITC-conjugated anti-CD56 antibody. In the figure, "FL1-Height" indicates the staining intensity with the FITC-conjugated anti-CD56 antibody. The dots in the region shown by "R2" (in the figure, the region surrounded by a square on the right side) indicate the cells stained with the FITC-conjugated anti-CD56 antibody. The dots in the region shown by "R3" (in the figure, the region surrounded by a square on the left side) indicate the cells not stained with the FITC-conjugated anti-CD56 antibody. (Example 2)

FIG. 2-B shows the result of flow-cytometer analysis of the lymph node with tumor of Dlg +/− mouse, indicating that the lymph node contains significantly increased number of cells stained with the FITC-conjugated anti-CD56 antibody. In the figure, "FL1-Height" indicates the staining intensity with FITC-conjugated anti-CD56 antibody. The dots in the region shown by "R2" (in the figure, the region surrounded by a square on the right side) indicate the cells stained with the FITC-conjugated anti-CD56 antibody. The dots in the region shown by "R3" (in the figure, the region surrounded by a square on the left side) indicate the cells not stained with the FITC-conjugated anti-CD56 antibody. (Example 2)

FIG. 3 shows the reduced expression of both sFRP1 and sFRP2 in an embryonic fibroblast (hereinafter, may be abbreviated to MEF) derived from Dlg −/− mouse compared to MEF derived from Dlg +/+ mouse. The analysis was carried out using an RNA sample extracted from each MEF by reverse transcription polymerase chain reaction (RT-PCR). Actin was used as an expression control. The MEFs (#33 primary and #44 primary) used herein were prepared from two strains of mice (#33 and #44). The immortalized MEF (#33 immortalized) used herein was prepared from the #33-derived MEF. These strains of mice were produced respectively from two clones that had been obtained by transfecting the targeting vector into an embryonic stem cell (may be abbreviated to ES cell). (Example 3)

FIG. 4 shows in the upper panel the examination result of Dlg expression in each cell by Western blotting, and shows in the lower panel the examination result of expression of each mRNA of actin (control), sFRP2 and sFRP1 by RT-PCR. In the figure, Dlg +/+MEF indicates Dlg +/+ mouse-derived immortalized MEF, Dlg −/− MEF indicates Dlg −/− mouse-derived immortalized MEF, and Dlg −/− MEF:Dlg indicates the cell prepared by transfecting Dlg −/− MEF with Dlg gene. The FIG. 4 demonstrates the following findings: Dlg +/+ MEF expressed Dlg and also expressed mRNAs for both sFRP2 and sFRP 1; on the other hand, Dlg −/− MEF showed no expression of Dlg and showed extremely low expression of sFRP mRNA in amount, particularly of sFRP2 mRNA, compared to Dlg +/+MEF; and transfection of Dlg −/− MEF with Dlg gene induced recovery of the expression of sFRP mRNA. (Example 3)

DETAILED DESCRIPTION OF THE INVENTION

Embodiments of the present invention are explained in further detail below.

In the present invention, Dlg gene knock-out mice were generated by means of genetic engineering techniques (see Example 1). Further, it was found for the first time in a mammal that the reduced expression and/or function of Dlg is an important factor for tumor formation The phrase "Dlg gene knock-out mice" means mice generated by making the individual deficient in only Dlg gene. The term "Dlg" means Dlg protein. The phrase "Dlg gene" means a gene encoding Dlg.

The term "expression" means that genetic information of DNA encoding a protein is transcribed into a mRNA, or that genetic information of DNA encoding a protein is transcribed into a mRNA and subsequently translated into an amino acid sequence of the protein. Namely, the phrase "expression of Dlg" means that genetic information of DNA encoding Dlg is transcribed into a Dlg mRNA, or that genetic information of DNA encoding Dlg is transcribed into a Dlg mRNA and subsequently translated into an amino acid sequence of Dlg. The phrase "expression of sFRP" means that genetic information of DNA encoding sFRP is transcribed into a sFRP mRNA, or that genetic information of DNA encoding sFRP is transcribed into a sFRP mRNA and subsequently translated into an amino acid sequence of sFRP.

Dlg gene knock-out mice with homozygous deficiency of Dlg gene (hereinafter, referred to as Dlg −/− mice) die shortly after birth, so that mature mice were not obtained, while embryo and new born mice were obtained. Dlg was not detected in Dlg −/− mice. Since Dlg −/− mouse is deficient in both of Dlg alleles, no transcription of Dlg gene occurs, which results in no expression of Dlg. Because of no expression of Dlg, Dlg −/− mice shows no function of Dlg. On the other hand, as for Dlg gene heterozygous deficient mice (hereinafter, referred to as Dlg +/− mice), embryo, new born mice, and mature mice were obtained. Dlg was detected in Dlg +/− mice, but the amount thereof was lower than that in wild mice (hereinafter, referred to as Dlg +/+ mice).

Dlg +/− mice showed formation of skin tumor and natural killer lymphoma along with the growth. In the skin tissue containing the tumor formed, Dlg was detected in a normal muscle cell, but not in a tumor cell. This finding suggests that the tumor formation in Dlg +/− mice may be due to the reduced expression and/or function of Dlg resulted from Dlg gene deficiency. Alternatively, it can be considered that natural mutation of Dlg gene may easily occur in Dlg +/− mice due to the deficiency in one of the alleles, which results in the abnormal expression of Dlg, and thereby causes tumor formation.

Further, a mouse embryonic fibroblast prepared from Dlg −/− mice showed a significant reduction of sFRP1 mRNA and sFRP2 mRNA, compared to a MEF prepared from Dlg +/+ mice. Particularly, the reduction was significant in sFRP2 mRNA. It was found that transfection of a Dlg −/− mice-derived MEF with Dlg gene for expression induced an increase of sFRP2 mRNA. This finding suggests that the reduction of sFRP1 mRNA and sFRP2 mRNA in a Dlg −/− mice-derived MEF may be due to Dlg gene deficiency. Reduction of mRNA induces reduction of a protein that is generated from the mRNA by translation, which results in reduced function of the protein in a living body.

The present inventors believe that the reduction in the expression and/or function of Dlg induces the reduction in the expression of sFRP, particularly the expression and/or function of sFRP2. sFRP is known to have a function as a Wnt antagonist and work for regulating the Wnt signal (Xu Q. et al., Development, 1998, Vol. 125, p. 4767-4776; and Chang J. T. et al., Human Molecular Genetics, 1999, Vol. 8, p. 575-583).

Recently, it was reported that restoration of the function of sFRP family such as sFRP2 in a colorectal cancer cell induced reduction of the Wnt signal (Non-Patent Reference 6). This report also discloses that sFRP gene methylation is observed in many colorectal cancer tissues. There results suggested the presence of a mechanism of colorectal cancer formation such that sFRP gene methylation induces the reduction in the expression and/or function of sFRP resulting in the activation of the Wnt signal transduction pathway. It has already been reported that methylation of many genes is observed in genome DNA of cancer cells, which indicates the relation of DNA methylation to carcinogenesis. DNA methylation is a reaction caused by DNA methyl transferase comprising the addition of a methyl group to DNA at cytosine residues to form 5-methyl cytosine. The methylated DNA is bound with MBP protein that is a protein capable of specifically binding to a methylated DNA, and then forms a complex with a transcriptional repressor including histone deacetylase, which results in deacetylation of histone. Consequently, chromatin structural change occurs and transcription is inhibited. Further, the binding of MBP protein inhibits demethylation of methylated DNA and maintains the methylated state, resulting in a stable inhibition of transcription. Namely, DNA methylation has a function of a switch for gene transcription. For example, methylation of tumor suppressor gene inhibits transcription of the gene, which may lead to oncogene transcription. Further, release of oncogene from methylation, the transcription of which is normally suppressed by methylation, may initiate the transcription of the oncogene.

Since sFRP has a function of regulating the Wnt signal, the mechanism of tumor formation due to Dlg gene deficiency can be considered to include a cascade in which the reduced expression and/or function of Dlg inhibits the expression and/or function of sFRP resulting in an increase of the Wnt signal. Namely, Dlg can be considered to be a factor located upstream of the Wnt signal transduction pathway regulated by sFRP, and to negatively regulate the Wnt signal by participating in the expression and/or function of sFRP. Therefore, the present inventors believe that Dlg inhibits the tumor formation due to the activation of the Wnt signal.

A mechanism of Dlg-related expression and/or function of sFRP can be considered that Dlg regulates transcription factors or transcriptional regulatory factors which relates to the expression of sFRP. Alternatively, the other mechanism can be considered that Dlg regulates sFRP gene methylation. For example of such a mechanism, it can be considered that Dlg inhibits the function of DNA methyltransferase working for sFRP gene methylation, and thereby maintains the expression and/or function of sFRP to be in a normal state.

Reduced expression and/or function of Dlg inhibit the expression and/or function of sFRP, resulting in an increase of the Wnt signal and in tumor formation. The inhibition of the expression and/or function of sFRP is caused not only by the reduced expression of Dlg and/or the reduced function of Dlg due to the reduction of the expression, but also by mutation of Dlg gene, abnormality in transcription/translation process of Dlg gene, reduced function of Dlg due to abnormality in protein modification process, or the like.

The expression and/or function of sFRP, preferably the expression and/or function of sFRP2, can be enhanced by enhancing the expression and/or function of Dlg. Consequently, it can be possible to inhibit the Wnt signal and to inhibit tumor formation. Further, it can be possible to prevent and/or treat a disease due to the activation of the Wnt signal, for, example, a tumor disease.

The term "function" means an inherent activity of a protein. In general, a protein exerts its function by contacting with the other substance, for example, the other protein to interact with. "Function of Dlg" can be, for example, an activity to enhance the expression and/or function of sFRP via regulation of the mechanism that relates to the expression and/or function of sFRP. "Function of sFRP" can be, for example, an activity as a Wnt signal antagonist to negatively regulate the Wnt signal transduction pathway.

The phrase "enhancing the expression and/or function of Dlg" means to alter a state where the expression and/or function of Dlg are almost not found to a state where the expression and/or function of Dlg are found. Further, the phrase also means to alter a state where the expression and/or function of Dlg are found to a state where the expression and/or function of Dlg are increased further.

The phrase "enhancing the expression and/or function of sFRP" means to alter a state where the expression and/or function of sFRP are almost not found to a state where the expression and/or function of sFRP are found. Further, the phrase also means to alter a state where the expression and/or function of sFRP are found to a state where the expression and/or function of sFRP are increased further.

A compound that exerts an enhancing effect on the expression and/or function of a certain protein, or a composition including the compound may be referred herein to as "enhancing agent".

The phrase "activation of the Wnt signal" means change in the extent of effect of the Wnt signal to be higher compared to a normal state. As a result of change in the extent of effect of the Wnt signal to be higher, cell proliferation, tumor formation, and the like, occurs.

The phrase "inhibiting the Wnt signal" means to reduce or eliminate the Wnt signal.

The phrase "inhibiting tumor formation" means to reduce or eliminate the generation and/or growth of tumor.

A compound that exerts an inhibitory effect on the expression and/or function of a certain protein, or a composition including the compound may be referred herein to as "inhibitor".

The term "compound" is used for indicating a chemical or biological compound. The chemical or biological compound is not particularly limited, and includes polypeptide, polynucleotide, DNA RNA, protein, antibody, low molecular weight compound, and the like.

The expression and/or function of Dlg can be enhanced, specifically, by using a compound having an effect of enhancing the expression and/or function of Dlg. Such a compound can be, for example, Dlg itself, Dlg gene or a recombinant vector containing Dlg gene. Alternatively, a compound having an effect of enhancing the expression and/or function of Dlg, which can be obtained by using an identification method of the compound constructed by employing a known pharmaceutical screening system, can be used as such a compound. A compound having an effect of enhancing the expression of Dlg can be obtained by using Dlg gene and an identification method generally used in screening a compound that enhances the expression of a gene, to select a compound having the effect from many compounds. A compound having an effect of enhancing the function of Dlg can be obtained using the function of Dlg, for example, the activity of enhancing the expression and/or function of sFRP as an index to select a compound having the effect from many compounds. Thus, a compound having an effect of enhancing the expression and/or function of Dlg can be used for enhancing the expression and/or function of sFRP, and thereby, allows the inhibition of Wnt signal-mediated cell proliferation and tumor formation, and further allows the prevention and/or treatment of a tumor disease.

The present invention provides an agent for enhancing the expression and/or function of sFRP, an agent for inhibiting tumor formation, and an agent for preventing and treating a tumor disease. All these agents comprise a compound having an effect of enhancing the expression and/or function of Dlg. The agent for inhibiting tumor formation can be an agent comprising the present enhancing agent. The agent for preventing and/or treating a tumor disease can be an agent comprising the present enhancing agent.

The present invention further provides a method of enhancing the expression and/or function of sFRP, a method of inhibiting tumor formation, and a method of preventing and treating a tumor disease. All of these methods comprise inhibiting the expression and/or function of Dlg. The present enhancing method can be conducted using a compound having an effect of enhancing the expression and/or function of Dlg. The method of inhibiting tumor formation can be conducted using any one of the aforementioned compound, the aforementioned enhancing agent, and the aforementioned enhancing method. The method of preventing and treating a tumor disease can be conducted using any one of the aforementioned compound, the aforementioned enhancing agent, and the aforementioned enhancing method.

sFRP of which expression and/or function is increased by the present invention may be preferably sFRP1 and sFRP2, and may be more preferably sFRP2.

A compound having an effect of enhancing the expression and/or function of Dlg may be preferably exemplified by Dlg itself, Dlg gene, or a recombinant vector containing Dlg gene.

Dlg can be a protein originating in all tissues, cells, and the like of a mammal such as human, mouse, rat, and the like. Specifically, for example, a human derived protein shown by the amino acid sequence set forth in SEQ ID NO: 2 in the sequence listing, or a mouse derived protein shown by the amino acid sequence set forth in SEQ ID NO: 4 can be preferably used. Dlg is not limited to the protein shown by the amino acid sequence set forth in SEQ ID NO: 2 or SEQ ID NO: 4, and can be a protein containing the amino acid sequence, or a protein shown by an amino acid sequence having a homology with the amino acid sequence of about 70% or more, preferably about 80% or more, more preferably about 90% or more, and even more preferably about 95% or more. Alternatively, Dlg can be a protein shown by an amino acid sequence with a mutation, such as a substitution, deletion, addition, insertion, or the like, of one or more amino acids in the amino acid sequence. The number of mutated amino acids is, for example from 1 to 100, preferably from 1 to 30, more preferably from 1 to 20, even more preferably from 1 to 10, and still more preferably from 1 to several in number. It is suitable for these proteins to have a function of Dlg, for example, to be capable of enhancing the expression and/or function of sFRP, preferably of sFRP2. The extent of mutation of amino acids, the position of a mutation, and the like, are not particularly limited as long as the protein with a mutation is capable of enhancing the expression and/or function of sFRP, preferably of sFRP2. Such a protein with a mutation may be a protein generated in nature, for example, due to mutation or post translational modification. Further, it may be a protein prepared by introducing a mutation into a natural gene. Techniques for introducing a mutation are known in the art. For example, known genetic engineering techniques can be used for preparing the protein. When introducing a mutation, in view of avoiding a change in the fundamental properties (such as physical properties, function, physiological activity, and immunological activity) of the protein, mutual substitution among homologous amino acids (polar amino acids, non-polar amino acids, hydrophobic amino acids, hydrophilic amino acids, positively-charged amino acids, negatively-charged amino acids and aromatic amino acids, or the like) may be readily conceived.

Dlg can be prepared from mammalian tissues or cells in which the expression of Dlg has been found, by purifying it using a known protein purification method. In such a procedure, at first, mammalian tissues or cells are homogenized and then subjected to extraction of a protein with acid, organic solvent, or the like. Subsequently, Dlg is isolated and purified from the obtained extract solution using a known purification method. An isolation/purification method is exemplified by ammonium sulfate precipitation, ultrafiltration, gel chromatography, ion-exchange chromatography, affinity chromatography, high performance liquid chromatography, and dialysis. These methods may be used independently or in suitable combinations. It is preferable to employ a method of specific absorption using a specific antibody to Dlg which is prepared using Dlg or its fragment by known antibody preparation method. Specifically, affinity chromatography that utilizes a column bound with specific antibodies can be used.

Dlg can also be produced according to conventional chemical synthesis methods. For example, methods described in the publications ("peptide synthesis", Maruzen Co., Ltd., 1975; and "peptide synthesis", Interscience, New York, 1996) can be used as chemical synthesis methods for proteins. However, chemical synthesis methods for proteins are not limited to the methods exemplified in the above, and any known methods can be used. Specifically, solid phase synthesis, solution phase synthesis, and the like, are known, and any of these methods can be used. More specifically, these kinds of protein synthesis methods include a so-called stepwise elongation method that sequentially binds each amino acid, one at a time, to elongate a chain based on the amino acid sequence information, and a fragment condensation method that previously synthesizes fragments consisting of several amino acids and subsequently subjects the respective fragments to a coupling reaction. Dlg can be synthesized by either of these methods. A condensation method used for the aforementioned protein synthesis methods can also be carried out according to conventional methods. Examples of condensation methods include an azide method, mixed anhydride method, DCC method, active ester method, oxidation-reduction method, DPPA (diphenylphosphoryl azide) method, DCC+ additive (1-hydroxybenzotriazole, N-hydroxysuccinamide, N-hydroxy-5-norbornane-2,3-dicarboxylmide, and the like) method, and Woodward's method. Dlg obtained by chemical synthesis can be suitably purified in accordance with various kinds of conventional purification methods as described above.

Dlg can also be produced based on the nucleotide sequence information of Dlg gene by using conventional genetic engineering techniques (Muramatsu Masami., Ed., "Labomanual Genetic Engineering", 1988, Maruzen Co., Ltd.; Ehrlich, H. A., Ed., PCR Technology. Principles and Applications for DNA Amplification, 1989, Stockton Press; and Ulmer, K. M. Science, 1983, Vol. 219, p. 666-671). For example, Dlg can be produced using a transformant transformed with a recombinant vector containing Dlg gene, by subjecting it to induction of Dlg expression and then collecting Dlg from the transformant. Further, as desired, Dlg can be purified from a cultured medium used for culturing the transformant or from the transformant, by the isolation/purification methods as described in the above. When Dlg is expressed in the transformant transformed with a recombinant vector containing Dlg gene or on its cell membrane, Dlg may be extracted from the disrupted transformant. Further, when Dlg is secreted outside the transformant transformed with a recombinant vector containing Dlg gene, the cultured medium can be used as it is, or the cultured medium after removing the transformant by centrifugation, and the like, can be used. Further, as desired, Dlg can be purified from a cultured medium used for culturing the transformant or from the transformant, by the isolation/purification methods as described in the above. Further, Dlg can be produced using a recombinant vector containing Dlg gene by employing a known cell free protein expression system (Madin, K. et al., Proceedings of The National Academy of Sciences of The United States of America, 2000, Vol. 97, p. 559-564).

Dlg gene is specifically exemplified by a human derived DNA shown by the nucleotide sequence set forth in SEQ ID NO: 1 in the sequence listing, or a mouse derived DNA shown by the nucleotide sequence set forth in SEQ ID NO: 3. Dlg gene is not limited to the DNA shown by the nucleotide sequence set forth in SEQ ID NO: 1 or SEQ ID NO: 3, and can be DNA containing the DNA, or DNA having a homology with the DNA of about 70% or more, preferably about 80% or more, more preferably about 90% or more, and even more preferably about 95% or more. Alternatively, Dlg gene can be DNA shown by a nucleotide sequence with a mutation, such as a substitution, deletion, addition, insertion, or the like, of one or more nucleotides in the nucleotide sequence, or by the complementary nucleotide sequence. The number of mutated nucleotides is, for example from 1 to 100, preferably from 1 to 30, more preferably from 1 to 20, even more preferably from 1 to 10, and still more preferably 1 to several in number. The extent of mutation, the position of a mutation, and the like, are not particularly limited as long as the DNA with a mutation encodes a protein having a function of enhancing the expression and/or function of sFRP. Such DNA with a mutation may be natural DNA, or may be DNA with an induced mutation. Further, it also may be DNA prepared by introducing a mutation into a natural gene. Techniques for introducing a mutation are known in the art, such as site-directed mutagenesis, genetic homologous recombination, primer extension, PCR, and the like. These methods can be used independently or in suitable combinations. For example, methods described in publications (Muramatsu Masami., Ed., "Labomanual Genetic Engineering", 1988, Maruzen Co., Ltd.; and Ehrlich, H. A., Ed., PCR Technology. Principles and Applications for DNA Amplification, 1989, Stockton Press) or modified methods thereof can be used for conducting the introduction of a mutation. In addition, Ulmer's techniques (Ulmer, K. M. Science, 1983, Vol. 219, p. 666-671) can also be utilized.

Dlg gene can be acquired by preparing a cDNA library in accordance with conventional methods from a suitable source in which the expression of Dlg was found, and then selecting a desired clone from the cDNA library. As a cDNA source, various kinds of cells and tissues in which the expression of Dlg was found, or cultured cells derived from these cells and tissues can be used. Since Dlg gene is expressed ubiquitously in many tissues and cells, various kinds of tissues and cells can be used for the cDNA source. For example, brain tissue, skin tissue, colon tissue, or the like, may be preferably used. Alternatively, cells derived from these tissues may be preferably used, as well. Isolation of total RNA from these sources, isolation and purification of mRNA, acquisition of cDNA and the cloning thereof, and the like, can each be performed in accordance with conventional methods. It is also possible to use a cDNA library that is constructed from commercially available polyA$^+$ RNA derived from human brain, fetal brain or cerebral hippocampus. A method of selecting a desired clone from a cDNA library is not particularly limited, and any of the methods generally used can be employed. For example, selection of a desired clone can be performed by using a probe or primer capable of selectively hybridizing to Dlg gene. Specifically, a plaque hybridization method, colony hybridization method, or the like, which uses a probe capable of selectively hybridizing to Dlg gene, or a combination of these methods can be employed. As a probe or a primer, a polynucleotide chemically synthesized based on the sequence information of Dlg gene can generally be used.

A recombinant vector containing Dlg gene can be prepared by inserting Dlg gene into a suitable vector DNA. The vector DNA is not particularly limited as long as it can be replicated within a host. The vector DNA can be suitably selected in accordance with the kind of host and purpose of use. The vector DNA may be vector DNA obtained by extracting natural DNA, or may be vector DNA that is deficient in a part of DNA other than a segment necessary for replication. Typical vector DNAs include, for example, vector DNA derived from a plasmid, a bacteriophage or a virus. A plasmid DNA is exemplified by a plasmid derived from *Escherichia coli*, a plasmid derived from *Bacillus subtilis*, or a plasmid derived from yeast. A bacteriophage DNA is exemplified by a λ phage. Vector DNA derived from a virus is exemplified by a vector derived from an animal virus such as a retrovirus, vaccinia virus, adenovirus, papovavirus, SV 40, fowlpox virus, and pseudorabies virus, or a vector derived from an insect virus such as baculovirus. Further, vector DNA derived from a transposon, an insertion element, a yeast chromosome element, or the like, may be used. Alternatively, vector DNA prepared by combining two or more of these, for example, vector DNA (cosmid, phagemid, or the like) prepared by combining genetic elements of a plasmid and a bacteriophage may be used. It is necessary for Dlg gene to be incorporated into vector DNA in such a way to allow the function of the gene to appear. The vector DNA contains at least Dlg gene and a promoter, as construction elements. In addition to these elements, as desired, a genetic sequence that encodes information relating to replication and control may be incorporated in combination into the vector DNA, by using a well-known method. Such a genetic sequence is exemplified by a ribosome binding sequence, terminator, signal sequence, cis element such as an enhancer, splicing signal, and a selective marker such as dihydrofolate reductase gene, ampicillin-resistant gene and neomycin-resistant gene. The vector DNA may contain one or more kinds of genetic sequences selected from the aforementioned members.

As a method of incorporating Dlg gene into vector DNA, any known methods can be employed. Specifically, a method may be used which comprises cleaving Dlg gene at specific sites, by treating it with suitable restriction enzymes, and then mixing it with a similarly treated vector DNA, for ligation using a ligase. Alternatively, a desired recombinant vector may be prepared by using a method that comprises ligating Dlg gene with a suitable linker, and then inserting it into the multi-cloning site of a vector suitable for the desired purpose.

A transformant prepared by transfecting a host with vector DNA into which Dlg gene was introduced is useful for producing a protein encoded by Dlg gene. Any prokaryotes and eukaryotes can be employed as a host. Examples of the prokaryotes include bacteria belonging to the *Escherichia* genus, such as, *Escherichia coli*, bacteria belonging to the *Bacillus* genus, such as, *Bacillus subtilis*, bacteria belonging to the *Pseudomonas* genus, such as, *Pseudomonas putida*, and bacteria belonging to the *Rhizobium* genus, such as, *Rhizobium meliloti*. Examples of the eukaryotes include yeasts, insect cells, and mammalian cells. Yeasts are exemplified by *Saccharomyces cerevisiae* and *Schizosaccharomyces pombe*. Insect cells are exemplified by Sf9 cells and Sf2 cells. Mammalian cells are exemplified by monkey kidney-derived cells such as COS cells, Vero cells, Chinese hamster ovary cell s(CHO cell), mouse L cells, rat GH3 cells, human FL cells, and human 293 EBNA cells. It is preferable to use mammalian cells. All known methods can be used for introducing vector DNA into a host. For example, a standard method described in publications (e.g. Muramatsu Masami., Ed., "Labomanual Genetic Engineering", 1988, Maruzen Co., Ltd.) may be utilized. When gene stability is a consideration, it is preferable to use a method that integrates the gene onto a chromosome. Meanwhile, it is convenient to use an autonomous replication system that utilizes an extranuclear gene. Specifically, calcium phosphate transfection, DEAE-dextran mediated transfection, microinjection, cationic lipid-mediated transfection, electroporation, transduction, scrape loading, ballistic introduction, infection, and the like, may be mentioned. When employing a prokaryote as a host, it is preferable to use a recombinant vector which is capable of autonomous replication within the bacterium and is also composed of a promoter, a ribosomal binding sequence, the polynucleotide of the present invention and a transcription termination sequence. It may also contain a gene that regulates the promoter. When employing bacteria as a host, any promoter may be used as long as it can lead to expression in bacteria such as *Escherichia coli*. For example, a promoter derived from *Escherichia coli* or a phage can be used, such as a trp promoter, lac promoter, PL promoter or PR promoter. An artificially designed and modified promoter such as a tac promoter may also be used. A method of introducing a recombinant vector into bacteria is not particularly limited, and any methods that introduce DNA into bacteria can be employed. Preferable examples of such a method include using calcium ions, electroporation, and the like. When employing a mammalian cell as a host, it is preferable to use the recombinant vector which is capable of autonomous replication within the cell and is also composed of a promoter, RNA splice site, a polynucleotide of the present invention, polyadenylated site and a transcription termination sequence. As desired, it may also contain an origin of replication. A SRα promoter, SV 40 promoter, LTR promoter, CMV promoter, and the like, can be used as a promoter. An early gene promoter of cytomegalovirus, and the like, may be used, as well. As a method of introducing the recombinant vector into a mammalian cell, preferably, for example, electroporation, the calcium phosphate technique, lipofection, or the like, may be used. A most preferable method to be used may be lipofection. When using yeast as a host, the promoter is not particularly limited as long as it can lead to an expression in yeast. Examples of such a promoter include the gall promoter, ga110 promoter, heat shock protein promoter, MFα1 promoter, PHO5 promoter, PGK promoter, GAP promoter, ADH promoter, and AOX1 promoter. A method of introducing a recombinant vector into yeast is not particularly limited as long as it is a method that introduces the DNA into the yeast. Preferable examples of such a method include electroporation, a spheroplast method, a lithium acetate method, or the like. When using an insect cell as a host, it is preferable to use a calcium phosphate technique, lipofection, or electroporation for a method of introducing a recombinant vector.

A compound having an effect of enhancing the expression and/or function of Dlg, can be obtained, for example, by an identification method using a Dlg gene deficient non-human mammal.

The present invention provides a method of identifying a compound comprising using a Dlg gene deficient non-human mammal. The Dlg gene deficient non-human mammal may be preferably a Dlg gene heterozygous deficient non-human mammal, and more preferable a Dlg gene heterozygous deficient mice.

The present identification method comprises administering a compound to be tested (hereinafter referred to a test compound) to a Dlg gene deficient non-human mammal, and measuring the expression and/or function of Dlg in the mammal, which allows to obtain a compound having an effect of enhancing the expression and/or function of Dlg.

When measuring the expression of Dlg and finding that the amount of expression of Dlg in a Dlg gene deficient non-human mammal subjected to administration of a test compound is increased compared to that in a Dlg gene deficient non-human mammal not subjected to administration of the test compound, it can be determined that the test compound has an effect of enhancing the expression of Dlg.

When measuring the function of Dlg and finding that the function of Dlg in a Dlg gene deficient non-human mammal subjected to administration of a test compound is increased compared to that in a Dlg gene deficient non-human mammal not subjected to administration of the test compound, it can be determined that the test compound has an effect of enhancing the function of Dlg. As the function of Dlg, for example, the function of enhancing the expression of sFRP can be mentioned. Therefore, a compound having an effect of enhancing the function of Dlg can be obtained by measuring the expression and/or function of sFRP in the present identification method. When finding that the expression and/or function of sFRP in a Dlg gene deficient non-human mammal subjected to administration of a test compound is increased compared to that in a Dlg gene deficient non-human mammal not subjected to administration of the test compound, it can be determined that the test compound has an effect of enhancing the function of Dlg.

The present identification method comprising measuring the expression and/or function of sFRP instead of measuring the expression and/or function of Dlg allows to obtain a compound having an effect of enhancing the expression and/or function of sFRP.

When measuring the expression of sFRP and finding that the amount of expression of sFRP in a Dlg gene deficient non-human mammal subjected to administration of a test compound is increased compared to that in a Dlg gene deficient non-human mammal not subjected to administration of the test compound, it can be determined that the test compound has an effect of enhancing the expression of sFRP.

When measuring the function of sFRP and finding that the function of sFRP in a Dlg gene deficient non-human mammal subjected to administration of a test compound is increased compared to that in a Dlg gene deficient non-human mammal not subjected to administration of the test compound, it can be determined that the test compound has an effect of enhancing the function of sFRP. As the function of sFRP, for example, the effect of inhibiting the Wnt signal transduction pathway can be mentioned. Therefore, a compound having an effect of enhancing the function of sFRP can be obtained by measuring the Wnt signal in the present identification method. When finding that the Wnt signal in a Dlg gene deficient non-human mammal subjected to administration of a test compound is reduced or eliminated compared to that in a Dlg gene deficient non-human mammal not subjected to administration of the test compound, it can be determined that the test compound has an effect of enhancing the function of sFRP.

The present identification method, comprising measuring tumor formation in a Dlg gene deficient non-human mammal instead of measuring the expression and/or function of Dlg, allows to obtain a compound having an effect of inhibiting tumor formation. When finding that the tumor formation in a Dlg gene deficient non-human mammal subjected to administration of a test compound is reduced or eliminated compared to that in a Dlg gene deficient non-human mammal not subjected to administration of the test compound, it can be determined that the test compound has an effect of inhibiting tumor formation. Measurement of tumor formation can be easily carried out by measuring the size, weight, and the like, of the tumor formed or of the tissue with tumor formed.

A compound having an effect of enhancing the function of Dlg obtained by the present identification method may be a compound having an effect of enhancing the function of sFRP, and a compound having an effect of inhibiting tumor formation. In addition, a compound having an effect of enhancing the function of sFRP may be a compound having an effect of inhibiting tumor formation.

Measurement of the expression of Dlg and sFRP can be carried out by measuring the transcription product of each of these genes, namely mRNA, or by measuring the translation product of the mRNA, namely protein. Any known gene detection methods can be used for measuring mRNA. Specifically, for example, Southern blotting, Northern blotting, the NASBA method (nucleic acid sequence-based amplification method), RT-PCR, plaque hybridization, colony hybridization, or the like, can be used. In addition, in situ RT-PCR, in situ hybridization, or the like, which allows cell level measurement can be used for the measurement. In such a gene detection method, it is useful for carrying out the measurement of a gene to use an oligonucleotide which consists of a partial sequence of the gene and has the property as a probe or a primer. The phrase "oligonucleotide having the property as a probe" means an oligonucleotide that is capable of specifically hybridizing only to the gene and consists of a characteristic sequence of the gene. The phrase "oligonucleotide having the property as a primer" means an oligonucleotide that is capable of specifically amplifying only a present polynucleotide, and consists of a characteristic sequence of a present polynucleotide. A probe and a primer may have a nucleotide sequence consisting of, preferably from about 5 to 50 nucleotides, more preferably from about 10 to 35 nucleotides, and further preferably from about 15 to 30 nucleotides. A labeled probe is normally used as the probe, but the unlabeled probe can also be used. Alternatively, the detection can also be carried out by measuring the specific binding to a ligand that was labeled directly or indirectly. Various methods are known for labeling a probe and a ligand. For example, nick translation, random priming, or a method utilizing kinase treatment may be used. Labeling substances suitable for use include a radioactive isotope, biotin, a fluorescent substance, a chemiluminescent substance, an enzyme, an antibody, and the like. PCR is preferable as a gene detection method from the viewpoint of sensitivity. Any well-known PCR methods can be employed using a primer capable of specifically amplifying Dlg gene or sFRP gene. For example, RT-PCR may be employed. In addition, various modified PCR methods used in the art can be employed. In addition to detection of a gene, PCR allows quantitative measurement of a gene. Such an assay method may be exemplified by a competitive assay, such as an MSSA method, (multi-channel simplex simulated annealing method), or PCR-SSCP, (PCR-single strand conformation polymorphism), which is known as a mutation detection method that utilizes a change in mobility accompanying a structural change of a single-stranded DNA.

Measurement of Dlg and sFRP can be carried out by employing a protein detection method or a protein quantitation method which is conventionally used. For example, Dlg and sFRP can be measured by carrying out immunoprecipitation using a specific antibody raised against Dlg or sFRP, and then analyzing with Western blotting or immunoblotting. Further, the detection of Dlg or sFRP in a paraffin tissue section or a frozen tissue section may be carried out by means of immuno-histochemical techniques using a specific antibody raised against Dlg or sFRP. The preferable methods of detecting Dlg or sFRP may be, for example, enzyme-linked immunosorvent assay (ELISA), radio immuno assay (RIA), immunoradiometric assay (IRMA), and immunoenzymometric assay (IEMA), including a sandwich method using a monoclonal antibody and/or a polyclonal antibody. Alternatively, competitive binding assay, and the like, may be employed.

Measurement of the function of Dlg can be carried out, for example, by measuring the enhancement of the expression of sFRP, since the function of enhancing the expression of sFRP is one of the functions of Dlg.

Measurement of the function of sFRP can be carried out, for example, by measuring the binding of sFRP to Wnt or an inhibitory effect of sFRP on Wnt signal activation, since sFRP binds to Wnt and shows the inhibitory effect. The binding of sFRP to Wnt can be measured by a conventional binding assay. The inhibitory effect on Wnt signal activation can be determined by measuring the expression of $\beta$-catenin that increases with Wnt signal activation and then detecting inhibition of the expression. The expression of $\beta$-catenin can be measured by a method similar to the method of measuring Dlg expression.

A route of administration of a test compound to a Dlg gene deficient non-human mammal may be systemic administration or local administration. Either route can be employed. For example, parenteral administration including normal intravenous injection and intraarterial administration can be employed. Oral administration can be also employed. A test compound may be, for example, a compound in a chemical library or natural products, and the like.

The method of identifying a compound according to the present invention can be conducted using a cell originating in a Dlg gene deficient non-human mammal instead of using the mammal. It may be preferable to use a cell that is found to be deficient in one or both of Dlg alleles, or a cell that is found to have a reduced expression and/or function of Dlg. It may be more preferable to use a cell that is found to be deficient in one of Dlg alleles. Analysis of the genotype of Dlg allele can be carried out, for example, by PCR or Southern blotting method, as described later. An embryonic fibroblast may be preferably used as the cell. Further, in the present invention, it can be possible to use an immortalized cell prepared from a cell originating in a Dlg gene deficient non-human mammal by using a well-known method. The preparation of an embryonic fibroblast from a mammal and the preparation of an immortalized cell can be carried out using known cell engineering techniques (Todaro G. J. et al., The Journal of Cell Biology, 1963, Vol. 17, p. 299-313).

The present identification method using a cell comprises contacting the cell with a test compound, and then measuring the expression of Dlg in the cell. Where the amount of expression of Dlg in a cell contacted with a test compound is increased compared to that in a cell not contacted with the test compound, it can be determined that the test compound has an effect of enhancing the expression of Dlg. When measuring the function of Dlg instead of measuring the expression of Dlg and finding that the function of Dlg in a cell contacted with a test compound is increased compared to that in a cell not contacted with the test compound, it can be determined that the test compound has an effect of enhancing the function of Dlg.

A cell originating in a Dlg gene deficient non-human mammal can be further used for conducting a method of identifying a compound having an effect of inhibiting methylation of sFRP gene and/or an effect of inducing demethylation of sFRP gene. The phrase "effect of inhibiting methylation of sFRP gene" means an effect of inhibiting the addition of a methyl group to sFRP gene at cytosine residues caused by DNA methyl transferase. The phrase "effect of inducing demethylation of sFRP gene" means an effect of removing the methyl group added to cytosine residues in sFRP gene. Both cells originating in a Dlg gene homozygous deficient non-human mammal and a Dlg gene heterozygous deficient non-human mammal can be used in the identification method of a compound having such an effect. A Dlg gene homozygous deficient mice show a significant reduction in the expression and/or function of sFRP compared to a Dlg gene heterozygous deficient mice. Therefore, it may be suitable to use preferably a cell originating in a Dlg gene homozygous deficient non-human mammal, more preferably a cell originating in Dlg gene homozygous deficient mice in such an identification method. The identification method comprises contacting the cell with a test compound, and then measuring methylation of sFRP gene in the cell. Where the amount of methylation of sFRP gene in a cell contacted with a test compound is reduced, compared to that in a cell not contacted with the test compound, it can be determined that the test compound has an effect of inhibiting methylation of sFRP gene and/or an effect of inducing demethylation of sFRP gene. Methylation of sFRP gene can be measured by a well-known method. For example, bisulfate sequencing method (Suzuki, H. et al., Nature Genetics, 2002, Vol. 31, p. 141-149), DMH (differential methylation hybridization) method using a micro array (Yan, P. S. et al., Clinical Cancer Research, 2000, Vol. 6, p. 1432-1438), methyl right method that is a real time PCR method using a fluorescent die (Trinh. B. N. et al., Methods, 2001, Vol. 25, p. 456-462) can be employed.

The present invention provides a Dlg gene deficient non-human mammal and a cell originating in the mammal. A Dlg gene deficient non-human mammal may be preferably a Dlg gene heterozygous deficient non-human mammal, and more preferably a Dlg gene heterozygous deficient mouse. A cell originating in a Dlg gene deficient non-human mammal may be preferably a cell that has been found to be deficient in one or both of Dlg allele, or to be reduced in the expression and/or function of Dlg. The cell may be more preferably a cell that has been found to be deficient in one of Dlg allele. Analysis of the genotype of Dlg allele can be carried out, for example, by PCR or Southern blotting method, as described later. An embryonic fibroblast may be preferably used as the cell. Further, an immortalized cell prepared from a cell originating in a Dlg gene deficient non-human mammal by using a well-known method is included in the scope of the present invention.

The phrase "Dlg gene deficient non-human mammal" means a mammal that was artificially made to be deficient in Dlg gene, and thereby to be eliminated or reduced in the expression of Dlg, which does not include human beings. A non-human mammal can by exemplified by a mouse, a rat, a hamster, a guinea pig, a bovine, a pig, a goat, or the like. It may be more preferably a mouse that is a rodent having relatively short ontogeny and biology cycle and is easily to breed. A Dlg gene deficient non-human mammal can be prepared using genetic engineering techniques such as a gene targeting method by converting Dlg gene in chromosome as desired (Gene targeting: a practical approach (Practical Approach Series 212), $2^{nd}$ Edition, 2000, Joyer, Alexandra L., Eds., published by Oxford University Print, etc.). The gene targeting method comprises preparing a construct (targeting vector) containing a Dlg gene incapable of expression by using an isolated gene from a genome library, and then transfecting it into an ES cell to obtain a Dlg gene mutant clone in which a homologous recombination has been occurred. The phrase "Dlg gene incapable of expression" means a Dlg gene that does not express Dlg when transfecting it into a cell or a living body, resulting from introduction of a mutation such as a mutation that inhibits the expression of Dlg or a mutation that causes deletion of the function of the protein encoded by Dlg gene. The introduction of a mutation in Dlg gene can be carried out using known genetic engineering techniques, by deleting a part or a full of the nucleotide sequence of Dlg gene, or by inserting of or substituting with the other gene. The introduction of such a mutation causes disruption of the function of a promoter or an exon, or causes shift of a codon reading frame, which results in allowing production of a knock out mouse with reduced or eliminated expression of Dlg. Examples of a gene used for introduction in order to disrupt the function of a promoter or an exon include a drug resistant gene such as a neomycin resistant gene and a hygromycin resistant gene, and the like. A neomycin resistant gene may be preferably used. In addition to the genes exemplified here, any genes normally used in the gene targeting method may be used. An Es cell can be established from a blastocyst of a non-human mammal. As a mouse ES cell, TT2 ES cell can be used, which was established from a blastocyst of the first filial generation of a cross between a C57BL/6 mouse and a CBA/JNCrj mouse. A Dlg gene mutant clone in which a homologous recombination has been occurred can be selected from ES cells which were transfected with a targeting vector by conducting a genotype analysis of the clones which were transfected with a targeting vector. PCR can be used for detecting deletion of Dlg gene by using as a primer an oligonucleotide consisting of a partial sequence of Dlg gene in the targeting vector or an oligonucleotide consisting of a partial sequence of a gene being introduced in order to disrupt the function of a promoter or an exon. The Southern blotting method allows detection of deletion in Dlg gene by determining the size of the DNA using a prove such as DNA sequence of Dlg gene or of the neighborhood of the gene. Alternatively, when a targeting vector was prepared using a drug resistant gene, a mutant clone can be easily selected by detecting drug resistance of the mutant clone. The thus obtained Dlg gene mutant clone allows generation of a chimera that is constructed with a cell having a normal Dlg gene locus and a cell having a mutated Dlg gene locus, by injecting it into a blastocyst or an eight cell stage embryo of a non-human mammalian embryo and then transplanting it into a uterus of a pseudo pregnant congenic non-human mammal. A heterozygous deficient individual with the introduced mutation in one of the homologous chromosomes or a homozygous deficient individual with the introduced mutation in both of the homologous chromosomes can be produced by mating the chimera with a wild type individual. Normally, such a mating results in production of a heterozygous deficient individual. A homozygous deficient individual can be produced by mating heterozygous deficient individuals with each other.

A compound obtained by the identification method according to the present invention, which has an effect of enhancing the expression and/or function of Dlg, may be used for an effective ingredient of an agent for enhancing the expression and/or function of Dlg, an agent for enhancing the expression and/or function of sFRP, an agent for inhibiting tumor formation, or an agent for preventing and/or treating a tumor disease. A compound obtained by the present identification method, which has an effect of enhancing the expression and/or function of sFRP, may be used for an effective ingredient of an agent for inhibiting tumor formation, or an agent for preventing and/or treating a tumor disease. A compound obtained by the present identification method, which has an effect of inhibiting tumor formation, may be used for an effective ingredient of an agent for preventing and/or treating a tumor disease. In addition, a compound obtained by the aforementioned identification method, which has an effect of inhibiting methylation of sFRP gene and/or an effect of inducing demethylation of sFRP gene, may be used for an effective ingredient of an agent for inhibiting methylation of sFRP gene and/or an agent for inducing demethylation of sFRP gene, an agent for enhancing the expression and/or function of sFRP, an agent for inhibiting tumor formation, or an agent for preventing and/or treating a tumor disease.

A compound obtained by the identification method according to the present invention and a medicament containing the compound as an effective ingredient are useful for elucidating the association of Dlg with the mechanism of suppression of tumor formation and for preventing and treating a tumor disease. Further, use of at least one of the compounds and medicaments allows execution of a method of enhancing the expression and/or function of Dlg, a method of inhibiting methylation of sFRP gene and/or a method of inducing demethylation of sFRP gene, a method of enhancing the expression and/or function of sFRP, a method of inhibiting tumor formation, or a method of preventing and/or treating a tumor disease. For example, a method of enhancing the expression and/or function of Dlg may be conducted by administering at least one of the aforementioned compounds and medicaments to a subject, or by contacting in vitro at least one of the aforementioned compounds and medicaments with a cell originating in a subject or a cultured cell, and the like. A method of inhibiting tumor formation or a method of preventing and/or treating a tumor disease may be conducted by administering at least one of the aforementioned compounds and medicaments to a subject.

The agent for enhancing the expression and/or function of Dlg, the agent for inhibiting methylation of sFRP and/or the agent for inducing demethylation of sFRP, the agent for enhancing the expression and/or function of sFRP, the agent for inhibiting tumor formation, or the agent for preventing and/or treating a tumor disease is preferably prepared as a pharmaceutical composition with one or more kinds of pharmaceutically acceptable carriers (pharmaceutical carriers). These medicaments can be used independently or in combination. An amount of the effective ingredient contained in the pharmaceutical composition can be suitably selected from a wide range. In general, a suitable amount may fall within a range of approximately 0.00001 to 70 wt %, preferably approximately 0.0001 to 5 wt %. A pharmaceutical carrier may be diluents and excipients, which are generally used in accordance with the form of use of the pharmaceutical composition, such as a filler, an extender, a binder, a wetting agent, a disintegrator, and/or a lubricant. These can be suitably selected and used in accordance with the form of use of the pharmaceutical composition used. The pharmaceutical carrier may be, for example, water, a pharmaceutically acceptable organic solvent, collagen, polyvinyl alcohol, polyvinylpyrrolidone, carboxyvinyl polymer, sodium alginate, soluble dextran, sodium carboxymethyl starch, pectin, xanthan gum, acacia gum, casein, gelatin, agar, glycerin, propylene glycol, polyethylene glycol, vaseline, paraffin, stearyl alcohol, stearic acid, human serum albumin, mannitol, sorbitol and lactose. One or a combination of two or more kinds of these carriers may be suitably selected and used in accordance with the form of use of the pharmaceutical composition of the present invention. As desired, various ingredients used in conventional protein preparations can be suitably used herein for preparing the pharmaceutical composition, such as a stabilizer, a bacteriocide, a buffer agent, an isotonizing agent, a chelating agent, a pH adjuster or a surfactant. As a stabilizer, the following may be used: human serum albumin, common L-amino acids, sugars and cellulose derivatives. These can be used independently or in combination with a surfactant, and the like. The use of these in such a combination may give increased stability to an effective ingredient. An L-amino acid is not particularly limited, and may be any one of glycine, cysteine, glutamic acid, and the like. A sugar is not particularly limited, and may be any one of the monosaccharides (such as glucose, mannose, galactose, and fructose), sugar alcohols (such as mannitol, inositol, and xylitol), disaccharides (such as sucrose, maltose, and lactose), polysaccharides (dextran, hydroxypropylstarch, chondroitin sulfate, and hyaluronic acid), derivatives thereof, and so on. A cellulose derivative is not particularly limited, and may be any one of methylcellulose, ethylcellulose, hydroxyethylcellulose, hydroxypropylcellulose, hydroxypropylmethylcellulose, sodium carboxymethylcellulose, and the like. A surfactant is not particularly limited, and can be both an ionic surfactant and a non-ionic surfactant. As a surfactant, the following may be used: polyoxyethyleneglycol sorbitan alkyl ester base; polyoxyethylene alkyl ether base; sorbitan monoacyl ester base; or a fatty acid glyceride base. As a buffer agent, the following may be used: boric acid; phosphoric acid; acetic acid citric acid; ε-aminocaproic acid; glutamic acid; and/or a salt thereof, for example, an alkali metal salt and/or an alkaline earth metal salt, such as a sodium salt, a potassium salt, a calcium salt and a magnesium salt. As an isotonizing agent, the following may be used: sodium chloride; potassium chloride; sugars or glycerin. As a chelating agent, sodium edentate and citric acid may be used.

The medicaments and the pharmaceutical compositions described in the above can be used as solution preparations. Alternatively, they can be freeze-dried, so as to be in a good state for preservation. They can be used by dissolving them in water, a buffered solution containing saline and the like, and then adjusting them to a suitable concentration, at the time of use.

Suitable dosage ranges of the medicaments and the pharmaceutical compositions described in the above are not particularly limited, and can be determined in accordance with the following: effectiveness of the ingredients contained therein; the administration form; the route of administration; the type of disease; the characteristics of the subject (e.g., body weight, age, symptomatic conditions, and whether a subject is taking other pharmaceutical agents); and the judgment of a physician in charge. In general, a suitable dosage may fall, for example, within a range of about 0.01 µg to 100 mg, per 1 kg of the body weight of the subject, and preferably within a range of about 0.1 µg to 1 mg, per 1 kg of the body weight. However, the dosage may be altered using conventional experiments for optimization of a dosage that are well known in the art. The aforementioned dosage can be divided for administration once to several times a day. Alternatively, periodic administration once every few days or few weeks can be employed.

The aforementioned medicaments or the aforementioned pharmaceutical compositions can be applied for a disease due to the reduced or eliminated expression and/or function of sFRP due to the reduced or eliminated expression and/or function of Dlg, for example, a tumor disease. In the case of application for a tumor disease, the type of a tumor being subjected to the application is not particularly limited. They can be applied for both solid tumors and non-solid tumors. Since Dlg gene is expressed ubiquitously in many tissues and cells, it can be considered that an abnormal expression of Dlg or a reduced function of Dlg due to a mutation, and the like induces tumor formation in a various kind of tissues and cells. Therefore, the types of solid tumors and non-solid tumors are not particularly limited as well. They can be applied for any kinds of tumors. Specifically, they can be applied for the solid tumors such as stomach cancer, esophageal cancer, colorectal cancer, small intestinal cancer, duodenum cancer, lung cancer, liver cancer, gall bladder cancer, pancreatic cancer, kidney cancer, urinary bladder cancer, oral cancer, bone cancer, skin cancer, breast cancer, uterus cancer, prostate cancer, brain tumor, neurofibroblastoma, and the like. Further, they can be applied for the non-solid tumors such as leukemia, malignant lymphoma, and the like. Preferably, they may be suitably applied for a tumor in which the reduced expression and/or function of Dlg, or a mutation of Dlg gene or Dlg has been found. More preferably, they may be suitably applied for skin cancer and lymphoma, since skin cancer and lymphoma was formed in Dlg +/− mice. When administering the aforementioned medicaments or the aforementioned pharmaceutical compositions, they can be used independently. Alternatively, they can be used in combination with the other compound or medicament required for preventing and/or treating the disease for which the present medicaments or the present pharmaceutical compositions are applied. For example, when using the aforementioned medicaments or the aforementioned pharmaceutical compositions in a method of preventing and/or treating a tumor disease, they can be used in combination with an agent for preventing and/or treating a tumor disease which is different from the medicaments or the pharmaceutical compositions.

In terms of a route of administration, it may be either systemic administration or local administration. The route of administration that is appropriate for a particular disease, symptomatic condition, or other factors, should be selected. For example, parenteral administration including normal intravenous injection, intraarterial administration, subcutaneous administration, intracutaneous administration, and intramuscular administration can be employed. Oral administration can be also employed. Further, transmucosal administration or dermal administration can be employed. In the case of use for a cancer disease, it is possible to employ a direct administration into the tumor by injection, and the like.

In terms of an administration form, various forms can be selected in accordance with a treatment purpose. For example, a solid formulation may be employed such as a tablet, pill, powder, powdered drug, fine granule, granule or a capsule. Alternatively, a liquid formulation can be employed such as an aqueous formulation, ethanol formulation, suspension, fat emulsion, liposome formulation, clathrate such as cyclodextrin, syrup or an elixir. These can be further classified, according to the administration route, into an oral formulation, parenteral formulation (drip injection formulation or injection formulation), nasal formulation, inhalant formulation, transvaginal formulation, suppositorial formulation, sublingual agents, eye drop formulation, ear drop formulation, ointment formulation, cream formulation, transdermal absorption formulation, transmucosal absorption formulation, and the like, which can be respectively blended, formed and prepared according to conventional methods.

A gene therapy agent, comprising as an effective ingredient Dlg gene or a transfection vector containing the gene, can be used for enhancing the expression and/or function of Dlg. The gene therapy agent may be a gene therapy agent comprising as an effective ingredient a cell into which the gene was introduced by the vector. A gene therapy agent is preferable to be prepared normally as injection formulation, drip injection formulation, or a liposome formulation. In the case that a gene therapy agent can be prepared as a form containing a cell with the gene introduced in it, it may be prepared as a form in which the cell is formulated in a phosphate buffered physiological saline (pH 7.4), Ringer's solution, or intracellular solution for injection formulation. A gene therapy agent can be prepared as a form that allows the administration in combination with the substance capable of enhancing transfection efficiency such as protamin, and the like. A gene therapy agent can be divided for administration once to several times a day. Alternatively, periodic administration once a day or few weeks can be employed. Suitable dosage ranges of a virus vector containing a desired gene may normally fall within a range of, for example, if using a retrovirus vector, about $1 \times 10^3$ pfu to $1 \times 10^5$ pfu per 1 kg of the body weight a day in terms of retrovirus titer. Further, when using a preparation containing a cell with a desired gene introduced in it, suitable dosage ranges may be selected from a range of about $1 \times 10^4$ cells/human to $1 \times 10^{15}$ cells/human. Treatment methods using a gene therapy agent include both methods of an in vivo method comprising introducing the aforementioned gene directly into the body, and an exo vivo method comprising introducing the gene in vitro into a target cell obtained from a patient's body and then bringing the cell back to the body. It is preferable to use in vivo method. As a method of introducing a gene into a body or a cell, both a non-viral transfection method and a transfection method utilizing a virus vector may be employed. A non-viral transfection method is more preferable, because it is superior in safety and in easiness and is low-cost compared to a method utilizing a virus vector. A non-viral transfection method may be exemplified by the following methods: a calcium phosphate co-precipitation method; a naked DNA method that comprises injecting a plasmid DNA directly into a target tissue in vivo; a cationic liposome method that comprises introducing a gene encapsuled in a multilamellar cationic liposome to a cell; a method, so called a gene gun, which comprises physically introducing plasmid DNA-coated gold into a cell by high pressure shootings; a method using a fusogenic liposome prepared by fusing an inactivated sendai virus with a liposome in which DNA is encapsuled; a method using a ligand-DNA complex that consists of DNA and a ligand capable of binding to a receptor expressed in a target tissue or a target cell; and a immunoliposome method that uses an immunoliposome prepared by binding an antibody capable of binding to a surface of a target tissue or a target cell to a surface of a liposome. Beside, a know transfection method that uses a polymer, a peptide, or the like, may be used. A non-viral transfection method is not limited to the methods exemplified in the above, and can be any methods as long as it allows transfection of a target gene or a target cell with a gene, without using a virus vector. A transfection method using a virus vector may preferably uses, for example, a retrovirus vector as a vector used for transfection. In addition to a retrovirus vector, an RNA virus vector, a DNA virus vector such as an adenovirus vector, an adeno-associated virus vector, a vaccinia virus vector, a herpes virus vector, and the like, may be used. The use of these virus vectors allows an efficient administration. Further, a transfection method using a virus vector that uses a liposome for administration in which a virus vector is encapsuled may be favorably employed. The use of a liposome allows an efficient transfer of a target substance to a target cell or a target tissue.

Therefore, it can be considered that a mixed treatment with a virus vector and liposome may show a high efficacy. In addition, it is known that a liposome is relatively stable and shows no major immune response in a treatment using a liposome, which suggests the usefulness of such a mixed treatment. A liposome may be preferably exemplified by a liposome prepared from cationic lipids. A transfection vector can be introduced into a cell by using a various kind of methods for introducing DNA into a cell which have been already known in the art, such as electroporation, calcium phosphate co-transfection method, viral transfection, or the like. A transformed cell itself can be utilized in an isolated condition as a model system for a research for pharmaceuticals and treatment. A gene to be introduced for producing a transfection vector can be obtained based on the nucleotide sequence information of Dlg gene by using conventional genetic engineering techniques as described in the above. A target tissue and a target cell to be transfected with a gene can be suitably selected for use in accordance with a subject of a gene therapy. A target cell is exemplified by a lymphocyte, fibroblast, hepatocyte, hemopoietic stem cell, and the like, but not limited thereto. Dlg gene can be introduced in any tissues and cells as long as the desired function of Dlg gene allows improvement and/or treatment of a target disease.

Diagnosis of a tumor disease can be conducted by detecting the expression and/or function of Dlg, because the reduced expression and/or function of Dlg were found to be an important factor in tumor formation.

The present invention provides a method of examining whether a test tissue is derived from a tumor tissue or a tumor cell, which comprises measuring the reduced expression and/or function of Dlg gene in a test tissue.

The present examination method comprise measuring the expression and/or function of Dlg gene in a specimen to be tested (test specimen), and detecting change of the expression and/or function, in comparison to a normal control specimen. Where the expression and/or function of Dlg is reduced or eliminated in comparison to a normal control specimen, it can be determined that the specimen is derived from a tumor tissue or a tumor cell.

The measurement of the expression of Dlg can be carried out by measuring the amount of RNA and/or cDNA derived from Dlg gene, or Dlg. The change of the presence or the change in amount of RNA and/or cDNA derived from Dlg gene, or Dlg can be detected in comparison to a normal control specimen. The measurement of the expression and/or function of Dlg can be carried out using the method described in the above.

The test specimen is not particularly limited, and any tissues and cells originated in living organism can be used. For example, a specimen derived from a living organism such as blood, urine, saliva, spinal fluid, biopsy tissue or autopsy material, and the like, may be used as a test specimen. As desired, a nucleic acid may be extracted from a test specimen to prepare a nucleic acid sample for use. A nucleic acid may be enzymatically amplified by employing PCR or other amplification methods. A nucleic acid sample may also be prepared according to various methods for facilitating detection of a target sequence, for example, denaturation, digestion with restriction enzyme, electrophoresis, or dot blotting.

Hereinafter, the present invention may be explained more specifically with the following examples.

EXAMPLE 1

Generation of Knockout Mice

<Materials and Methods>

1. Construction of a Targeting Vector

A genomic mouse Dlg (mDlg) DNA was isolated from a TT2 genomic library by screening with an amino-terminal region (amino acids 1-112) of the mDlg cDNA. The isolated clone was subcloned into the EcoRI site of pBluescript II (Stratagene). Targeting was designed to replace the BamHI-XhoI region of the mDlg gene with the neomycin resistant gene. The short arm of homology was a 0.8-kb BamHI-ClaI genomic fragment of midstream of exon 2, and the long arm was a 9.5-kb ClaI-XhoI fragment. The neomycin resistant gene without promoter and polyadenylation signal was inserted into the ClaI site of the mDlg fragment by blunt-end ligation and in-frame fusion. The vector was subcloned into pBluescript II and linearized with NotI.

2. ES cells and Transfection

TT2 ES cells were established from the first filial generation (F1) blastocyst between C57BL/6 and CBA/JNCrj mice and cultured on feeder cells. As the feeder cells, mitomycin C (Sigma)-treated primary fibroblasts prepared from E14 mouse embryos were used. As the culture medium, a culture medium with a following composition was used: Dulbecco's modified Eagle's medium (DMEM) (NISSUI) supplemented with 15% Serum Replacement (Gibco BRL), 1000 U/ml leukemia inhibitory factor (Gibco BRL), 0.1 mM 2-mercaptoethanol (Sigma), and 1× non-essential amino acids (Gibco BRL). TT2 ES cells ($2\times10^7$ cells) in 0.4 ml of phosphate buffered physiological saline (PBS) were transfected with 50 μg of NotI-linearized targeting vector by electroporation using a Bio-Rad Gene Pulsar (set at 800 V and 3.0 mFD). The obtained cells were plated in several dishes, and then positive selection using 150 μg/ml of G418 was started from the following day. Ten days after the electroporation, colonies were picked up and trypsinized; 80% of the cell suspension was plated on new feeder cells, and the rest was subjected to PCR analysis to detect mDlg recombinant clones. PCR was performed for 30 cycles using EX taq polymerase (TaKaRa); each cycle consisted of denaturation at 94° C. for 1 min, annealing at 60° C. for min, and polymerization at 72° C. for 3 min. The sequence of the sense primer and the antisense primer were shown in below.

```
sense primer:
5'-ATGCCGGTCCGGAAGCAAGA-3'      (SEQ ID NO: 5)

antisense primer:
5'-TCTTCATCCTGATACCTGTA-3'      (SEQ ID NO: 6)
```

3. Generation of Chimeras

The generation of chimeras was carried out according to the method described in publications ("Gene Targeting: Generation of a mutant mouse using an ES cell (Biomanual series 8)" Shinichi Aizawa, Yodosha, p. 119-134; etc.). Specifically, chimeras were generated by injecting about ten ES cells treated as above into a single 8-cell stage ICR mouse embryo and transplanting the embryos into the uterus of pseudo-pregnant females. Genotypes of the obtained mice were determined by the method described later. After that, Dlg +/+ mice, Dlg +/− mice and Dlg −/− mice were generated by mating.

4. Genotyping of Wild-type and Mutant Alleles

Genotypes of newborn and adult mice were routinely assessed by PCR analyses. The wild-type allele was identified as a 503-bp product in PCR analysis with primers in the sense (5'-GCTGTCAGTCCACAGCTAACACAGGCTACT-3' (SEQ ID NO: 7)) and antisense (5'-TGTCCTAAGTTAAG-GACCATCTAGAGAGCC-3' (SEQ ID NO: 8)) oligonucleotides of the mDlg gene. The mutant allele was identified as a 273-bp product in PCR analysis with a primer in the sense strand oligonucleotide (5'-TCGTGCTTTACGGTATCGC-CGCTCCCGATT-3' (SEQ ID NO: 9)) of the neomycin resistant gene and the antisense oligonucleotide (SEQ ID NO: 8) of the mDlg gene.

For Southern blot analysis, 10 μg of DNA derived from tails of newborn mice was digested with EcoRI, electrophoresed on a 0.8% agarose gel, blotted onto nitrocellulose filter (Hybond-N+; Pharmacia), and hybridized with digoxigenin labeled 5' probe.

5. Analysis of Dlg Protein Expression

New born mice brain lysates were subjected to SDS-PAGE followed by immuno blotting with anti-Dlg antibody. Specifically, brains were collected from new born mice and homogenized with an appropriate volume of lysis buffer (Tris (pH 7.4) 100 mM, NaCl 150 mM, 1% Triton, NaF 50 mM, $Na_2MoO_4$ 50 μM, $Na_3VO_4$ 1 mM, aprotinin 10 μg/ml, leupeptin 10 μg/ml). Then, centrifugation was carried out at 15,000 rpm for 20 min at 4° C. to collect the supernatant for use as brain lysates. The brain lysates were subjected to SDS-PAGE with 6% polyacrylamide gel. Gel and membrane (Immobilon-P, MILLIPORE) were sandwiched with each four filter papers soaked with transfer buffer (glycine 2.92 g, Tris 5.81 g, SDS 0.375 g, methanol 200 ml/1000 ml), and then subjected to the current of 1.4 mA/cm² filter paper for 1 hr for transfer. The membrane was subjected to blocking for 30 min in Tris buffered physiological saline (TBS) containing 5% skim milk. The Dlg antibody (Transduction) diluted with TBS containing 5% skim milk was dropped down on the membrane and incubated for 1 hr. After washing with TBS containing 0.1% Tween for 5 min, alkaline phosphatase-conjugated anti-mouse IgG antibody (Promega) diluted with TBS was dropped down on the membrane and incubated for 30 min. After washing with TBS containing 0.1% Tween for 5 min, the membrane was soaked in AP buffer (Tris 100 mM, NaCl 100 ml, $MgCl_2$ 5 mM) containing NBT/BCIP (Promega) for color development to detect the expression of Dlg.

<Results>

FIG. 1-A shows Dlg Locus, targeting vector construct, and Dlg gene introduced by homologous recombination.

FIG. 1-B shows results of Southern blot analysis of tail DNA from each mouse of the third filial generation using 5' probe. In Dlg +/+ mice, only an internal EcoRI fragment was detected. In Dlg −/− mice, only a mutated EcoRI fragment was detected. In Dlg +/− mice, both an internal EcoRI fragment and a mutated EcoRI fragment were detected.

FIG. 1-C shows results of genotyping of each mouse of the third filial generation using tail DNA from each mouse. The genotype of the alleles was found to be wild-type in Dlg +/+ mice and mutant in Dlg −/− mice. In addition, it was found that Dlg +/− mice have both alleles of wild-type and mutant.

FIG. 1-D shows analysis results of the expression of Dlg in each mouse of the third filial generation. Dlg was detected in Dlg +/+ mouse and Dlg +/− mouse. The amount of Dlg detected in Dlg +/− mouse was less than that in Dlg +/+ mouse. In contrast, Dlg was not detected in Dlg −/− mouse.

Thus, Dlg +/− mice and Dlg −/− mice were obtained by using the aforementioned targeting vector. An embryo, newborn mice, and adult mice were obtained for Dlg +/− mice. On the other hand, no adult mice were obtained for Dlg −/− mice, because of its death shortly after birth: however, an embryo and newborn mice were obtained. Dlg +/− mice showed the reduced expression of Dlg, while Dlg −/− mice showed no expression of Dlg.

EXAMPLE 2

Dlg +/− mice showed tumor formation in skin and lymph nodes along with the growth. These tumors were subjected to the following analysis.

<Method>

1. Immuno-Histochemical Analysis

Skin tumor tissues of Dlg +/− mice were used for preparing tissue sections in accordance with a conventional method. The tissue sections were subjected to DAB staining. Specifically, the tissue sections were formalin-fixed and paraffin-embedded. After blocking in Supermix (0.25% gelatin and 0.5% Triton X-100) overnight, the sections were incubated overnight with anti-cytokeratin AE1/AE3 antibody and anti-Dlg antibody, washed three times in PBS for 10 min. Then, the sections were incubated for 1 hr with biotinylated anti-mouse rabbit IgG and anti-rabbit goat IgG (Vector) diluted to 1/250 with Supermix. The sections were then washed four times in PBS for 10 min, incubated with the ABC reaction mixture (Elite ABC Kit; Vector, PK-6100) diluted to 1/400 with Supermix for 1 hr. Subsequently, the sections were washed three times in PBS for 10 min and incubated for 5 min with DAB solution (0.2 mg/ml DAB, 3 mg/ml Nickel ammonium 0.0045% $H_2O_2$ in PBS). All incubations were performed at room temperature.

2. Hematoxilin-Eosin Staining

Lymph nodes of Dlg +/− mice were used for preparing tissue sections in accordance with a conventional method. The tissue sections were subjected to hematoxilin-eosin staining.

3. Analysis by Flow Cytometry

Cervical lymph nodes were excised from Dlg +/− mice that showed tumor formation. Lymph node cells were prepared from the lymph nodes by mincing softly to dissect the tissue and filtering through a 100 μm mesh filter to remove tissue fragments and cell aggregates. Lymph node cells prepared from cervical lymph nodes of Dlg +/+ mice in a same manner were used as a control for comparison. The obtained cells were stained with fluorescein isothiocyanate (FITC)-conjugated anti-CD56 antibody and analyzed by flow cytometry in a FACScan flow cytometer.

<Results>

The skin tumor tissue sections of Dlg +/− mice were partially positive with cytokeratin AE1/AE3 staining. The tumor that was formed was considered to be poroid hidradenoma that was derived from skin epithelial cells. The skin tumor tissue sections showed Poroid hidradenoma cells not stained with anti-Dlg antibody, but showed muscle stained with anti-Dlg antibody.

The tumor formation was detected in the tissue sections of the lymph nodes of Dlg +/− mice by hematoxilin-eosin staining. In addition, a significant increase of the cells being stained with FITC-conjugated anti-CD56 antibody was found in the cells prepared from the cervical lymph nodes of Dlg +/− mice that showed tumor formation (FIG. 2-B), compared to that in the cells prepared from the lymph nodes of Dlg +/+ mice (FIG. 2-A). FIG. 2-A and FIG. 2-B showed the cells being stained with FITC-conjugated anti-CD56 antibody as the dots in the region shown by "R2" (in the figure, the region surrounded by a square on the right side). The dots in R2 are significantly more in FIG. 2-A compared to in FIG. 2-B, which revealed that the cells being stained with FITC-conjugated anti-CD56 antibody was significantly increased in the lymph nodes of Dlg +/− mice. The cells being stained with FITC-conjugated anti-CD56 antibody were observed in approximately 0.10% of the lymph node cells of Dlg +/− mice, while those were observed in approximately 66.03% of the lymph node cells of Dlg +/− mice that showed tumor formation. These findings revealed that Dlg +/− mice formed lymphoma that contained cells having CD56 antigens on the cell surface in lymph nodes. It was considered that the lymphoma formed was natural killer lymphoma because it has CD56 antigen on the cell surface.

These results revealed that Dlg +/− mice formed skin tumor and lymphoma. Dlg was expressed in normal cells in skin tissue in which tumor was formed. In contrast, Dlg was not expressed in tumor cells. Therefore, the reduced expression and/or function of Dlg can be considered to be an important factor for tumor formation.

Thus, it was found that Dlg gene deficiency led to the reduced expression and/or function of Dlg resulting in formation of tumor such as skin tumor, lymphoma, and the like.

EXAMPLE 3

In order to examine the mechanism of tumor formation due to Dlg deficiency, it was conducted to search for a gene of which expression changes due to Dlg deficiency. The search for a gene was carried out by a conventional micro array method using mouse embryonic fibroblasts (MEFs) derived from Dlg +/+ mice and Dlg −/− mice which were generated in Example 1. As a result, Dlg −/− mice derived MEFs showed reduction in sFRP1 mRNA and in sFRP2 mRNA. Then, further analysis for changes in sFRP gene and in sFRP2 gene was carried out by RT-PCR.

<Materials and Methods>

1. Cells and Culture

Mouse embryonic fibroblasts (MEFs) were obtained from 13.5-day-old embryos of Dlg +/+ mice and Dlg −/− mice. Immortalized MEFs were generated from primary MEFs by an established procedure (Todaro G. J. et al., The Journal of Cell Biology, 1963, Vol. 17, p. 299-313). MEFs were maintained in DMEM containing 10% fetal bovine serum (FBS) and antibiotics.

2. Enrichment of Dlg-transfected MEFs by Auto-MACS

Dlg −/− immortalized MEFs were transfected with Dlg by using the pMKitneo-Dlg vector that allows the expression of mouse Dlg gene. To selectively enrich for Dlg-transfected MEFs, Dlg −/− immortalized MEFs were co-transfected with the pMKitneo-Dlg vector and the pMACS $k^k$ II vector that allows the expression a truncated H2-$k^k$ molecule (the nucleotide sequence of the gene was set forth in SEQ ID NO: 10). MEFs were harvested 24 h after co-transfection, re-suspended in PBE (PBS with 5 mM ethylenediamine tetra-acetic acid (EDTA)) buffer, and incubated with MACSelect $k^k$ microbeads for 15 min followed by magnetic separation.

3. RT-PCR Analysis

Total RNA was extracted from MEFs using ISOGENE (Nippon Gene). Total RNA (5 μg) was used to produce cDNA using Superscript III reverse transcriptase (Invitrogen) according to manufacturer's protocol. The PCR cycling parameters are 94° C. for 1 min; then followed by 30 cycles at 94° C. for 30 sec, 55° C. for 30 sec and 72° C. for 1 min with a final extension at 72° C. for 10 min after the last cycle.

<Results>

MEFs (#33 primary and # 44 primary) were generated from two mouse lines (#33 and #44). The mouse lines #33 and #44 were, respectively, generated using clones obtained from different dishes among several dishes in which cells transfected with targeting vector by electroporation were plated and subjected to drug selection. As for #33 derived MEFs, immortalized MEFs were also generated. RNA samples respectively extracted from Dlg +/+MEFs and Dlg −/− MEFs were examined for sFRP1 and sFRP2 expression by RT-PCR. They were also examined for the expression of actin in the same manner for control.

These three distinctive Dlg −/− MEFs showed reduced expression of sFRP mRNA and sFRP2 mRNA compared to Dlg +/+MEFs (FIG. 3). The reduction was more significant in sFRP2 mRNA than in sFRP1 mRNA. There was no difference in amount of actin mRNA.

RNA samples respectively extracted from Dlg +/+immortalized MEFs, Dlg −/− immortalized MEFs and Dlg-transfected Dlg −/− immortalized MEFs were examined for sFRP2 and sFRP1 expression by RT-PCR. In addition, detection of Dlg was carried out for each cell by western blotting. As a result, Dlg was detected in Dlg +/+ immortalized MEFs, but not detected at all in Dlg −/− immortalized MEFs. In contrast, Dlg was detected in Dlg-transfected Dlg −/− immortalized MEFs (FIG. 4). sFRP2 mRNA was significantly reduced in Dlg −/− immortalized MEFs compared to in Dlg +/+ immortalized MEFs (FIG. 4). sFRP2 mRNA in Dlg-transfected Dlg −/− immortalized MEFs was increased compared to in Dlg non-transfected one (FIG. 4).

These results revealed that Dlg deficiency led to inhibition of the expression of sFRP1 and sFRP2, particularly of sFRP2. In addition, it was found that Dlg transfection allowed enhancement of the sFRP2 expression.

INDUSTRIAL APPLICABILITY

The present invention is useful for the purpose of molecular-level elucidation of the mechanism of tumor formation such as the formation of skin tumor or lymphoma. Further, the present invention can be utilized in developing an agent for or a method of inhibiting tumor formation, and in developing an agent for or a method of preventing or treating a cancer disease. Thus, the present invention is extremely useful in a field for pharmaceutical research, pharmaceutical development and so on.

GENERAL DESCRIPTION OF THE SEQUENCES

SEQ ID NO: 1: human Dlg (discs large) gene

SEQ ID NO: 2: human Dlg (discs large)

SEQ ID NO: 3: mouse Dlg (discs large) gene

SEQ ID NO: 4: mouse Dlg (discs large)

SEQ ID NO: 5: a designed oligonucleotide for use as a primer.

SEQ ID NO: 6: a designed oligonucleotide for use as a primer.

SEQ ID NO: 7: a designed oligonucleotide for use as a primer.

SEQ ID NO: 8: a designed oligonucleotide for use as a primer.

SEQ ID NO: 9: a designed oligonucleotide for use as a primer.

SEQ ID NO: 10: H2-$k^k$ gene.

What is claimed is:

1. A method of identifying a compound having an effect of enhancing expression and/or function of sFRP (secreted frizzled-related protein), comprising:
   a) providing a mouse that is deficient in both of Dlg (discs large) alleles;
   b) administering a test compound to the mouse; and
   c) measuring expression and/or function of sFRP.

2. A method of identifying a compound having an effect of enhancing expression and/or function of sFRP (secreted frizzled-related protein), comprising:
   a) providing a cell originating in a mouse that is deficient in both of Dlg alleles;
   b) contacting a test compound with the cell; and
   c) measuring expression and/or function of sFRP.

3. The method according to claim 1, wherein sFRP is sFRP2.

4. The method according to claim 2, wherein sFRP is sFRP2.

5. A method of identifying a compound that inhibits tumor formation, comprising:
   a) providing a mouse that is deficient in both of Dlg (discs large) alleles;
   b) administering a test compound to the mouse;
   c) measuring expression and/or function of sFRP, and
   d) testing or utilizing said test compound for inhibition of tumor formation if said compound has an effect of enhancing expression and/or function of sFRP.

6. A method of identifying a compound that inhibits tumor formation, comprising:
  a) providing a cell originating in a mouse that is deficient in both of Dlg alleles;
  b) contacting a test compound with the cell;
  c) measuring expression and/or function of sFRP, and
  d) testing or utilizing said test compound for inhibition of tumor formation if said compound has an effect of enhancing expression and/or function of sFRP.

7. The method according to claim 5, wherein sFRP is sFRP2.

8. The method according to claim 6, wherein sFRP is sFRP2.

* * * * *

SEQUENCE LISTING

<160> NUMBER OF SEQ ID NOS: 10

<210> SEQ ID NO 1
<211> LENGTH: 2980
<212> TYPE: DNA
<213> ORGANISM: Homo sapiens
<220> FEATURE:
<221> NAME/KEY: misc_feature
<223> OTHER INFORMATION: human Dlg(discs large) gene

<400> SEQUENCE: 1

```
gttggaaacg gcactgctga gtgaggttga ggggtgtctc ggtatgtgcg ccttggatct      60
ggtgtaggcg aggtcacgcc tctcttcaga cagcccgagc cttcccggcc tggcgcgttt     120
agttcggaac tgcgggacgc cggtgggcta gggcaaggtg tgtgccctct tcctgattct     180
ggagaaaaat gccggtccgg aagcaagata cccagagagc attgcacctt ttggaggaat     240
atcgttcaaa actaagccaa actgaagaca gacagctcag aagttccata gaacgggtta     300
ttaacatatt tcagagcaac ctctttcagg ctttaataga tattcaagaa ttttatgaag     360
tgaccttact ggataatcca aaatgtatag atcgttcaaa gccgtctgaa ccaattcaac     420
ctgtgaatac ttgggagatt ccagccttc aagctctac tgtgacttca gagacactgc     480
caagcagcct tagccctagt gtagagaaat acaggtatca ggatgaagat acacctcctc     540
aagagcatat ttccccacaa atcacaaatg aagtgatagg tccagaattg gttcatgtct     600
cagagaagaa cttatcagag attgagaatg tccatggatt tgtttctcat tctcatattt     660
caccaataaa gccaacagaa gctgttcttc cctctcctcc cactgtccct gtgatccctg     720
tcctgccagt ccctgctgag aatactgtca tcctacccac cataccacag gcaaatcctc     780
ccccagtact ggtcaacaca gatagcttgg aaacaccaac ttacgttaat ggcacagatg     840
cagattatga atatgaagaa atcacacttg aaagggaaaa ttcagggctt ggtttcagca     900
ttgcaggagg tacggacaac ccacacattg agatgactc aagtattttc attaccaaaa     960
ttatcacagg gggagcagcc gcccaagatg aagattgcg ggtcaatgac tgtatattac    1020
aagtaaatga agtagatgtt cgtgatgtaa cacatagcaa agcagttgaa gcgttgaaag    1080
aagcagggtc tattgtacgc ttgtatgtaa aagaaggaa accagtgtca gaaaaaataa    1140
tggaaataaa gctcattaaa ggtcctaaag gtcttgggtt tagcattgct ggaggtgttg    1200
gaaatcagca tattcctggg gataataagca tctatgtaac caaaataatt gaaggaggtg    1260
cagcacataa ggatggcaaa cttcagattg gagataaact tttagcagtg aataacgtat    1320
gtttagaaga agttactcat gaagaagcag taactgcctt aaagaacaca tctgattttg    1380
tttatttgaa agtggcaaaa cccacaagta tgtatatgaa tgatggctat gcaccacctg    1440
atatcaccaa ctcttcttct cagcctgttg ataaccatgt tagcccatct tccttcttgg    1500
gccagacacc agcatctcca gccagatact ccccagtttc taaagcagta cttggagatg    1560
atgaaattac aagggaacct agaaaagttt tcttcatcg tggctcaacg ggccttggtt    1620
tcaacattgt aggaggagaa gatggagaag gaatatttat ttcctttatc ttagccggag    1680
gacctgctga tctaagtgga gagctcgaa aaggagatcg tattatatcg gtaaacagtg    1740
ttgacctcag agctgctagt catgagcagg cagcagctgc attgaaaaat gctggccagg    1800
ctgtcacaat tgttgcacaa tatcgacctg aagaatacag tcgttttgaa gctaaaatac    1860
atgatttacg ggagcagatg atgaatagta gtattagttc agggtcaggt tctcttcgaa    1920
```

-continued

```
ctagccagaa gcgatccctc tatgtcagag cccttttga ttatgacaag actaaagaca    1980
gtgggcttcc cagtcaggga ctgaacttca aatttggaga tatcctccat gttattaatg   2040
cttctgatga tgaatggtgg caagccaggc aggttacacc agatggtgag agcgatgagg   2100
tcggagtgat tcccagtaaa cgcagagttg agaagaaaga acgagcccga ttaaaaacag   2160
tgaaattcaa ttctaaaacg agagataaag gggagatccc tgacgacatg ggatcaaaag   2220
gcctgaagca tgtaacttct aatgccagcg atagtgaaag tagttaccgt ggtcaagaag   2280
aatacgtctt atcttatgaa ccagtgaatc aacaagaagt taattatact cgaccagtga   2340
tcatattggg acctatgaaa gacaggataa atgatgactt gatctcagaa tttcctgaca   2400
aatttggatc ctgtgttcct catacaacta gaccaaaacg agattatgag gtagatggaa   2460
gagattatca ttttgtgact tcaagagagc agatggaaaa agatatccag gaacataaat   2520
tcattgaagc tggccagtat aacaatcatc tatatggaac aagtgttcag tctgtacgag   2580
aagtagcagg aaagggcaaa cactgtatcc ttgatgtgtc tggaaatgcc ataaagagat   2640
tacagattgc acagctttac cctatctcca tttttattaa acccaaatcc atggaaaata   2700
tcatggaaat gaataagcgt ctaacagaag aacaagccag aaaaacattt gagagagcca   2760
tgaaactgga acaggagttt actgaacatt tcacagctat tgtacagggg gatacgctgg   2820
aagacattta caaccaagtg aaacagatca tagaagaaca atctggttct acatctgggg   2880
ttccggcaaa agaaaagcta tgaaaactca tgtttctctg tttctctttt ccacaattcc   2940
attttctttg gcatctcttt gcccttcct ctggaaaaaa                          2980
```

<210> SEQ ID NO 2
<211> LENGTH: 904
<212> TYPE: PRT
<213> ORGANISM: Homo sapiens
<220> FEATURE:
<221> NAME/KEY: misc_feature
<223> OTHER INFORMATION: human Dlg(discs large)

<400> SEQUENCE: 2

```
Met Pro Val Arg Lys Gln Asp Thr Gln Arg Ala Leu His Leu Leu Glu
 1               5                  10                  15

Glu Tyr Arg Ser Lys Leu Ser Gln Thr Glu Asp Arg Gln Leu Arg Ser
                20                  25                  30

Ser Ile Glu Arg Val Ile Asn Ile Phe Gln Ser Asn Leu Phe Gln Ala
            35                  40                  45

Leu Ile Asp Ile Gln Glu Phe Tyr Glu Val Thr Leu Leu Asp Asn Pro
        50                  55                  60

Lys Cys Ile Asp Arg Ser Lys Pro Ser Glu Pro Ile Gln Pro Val Asn
65                  70                  75                  80

Thr Trp Glu Ile Ser Ser Leu Pro Ser Ser Thr Val Thr Ser Glu Thr
                85                  90                  95

Leu Pro Ser Ser Leu Ser Pro Ser Val Glu Lys Tyr Arg Tyr Gln Asp
                100                 105                 110

Glu Asp Thr Pro Pro Gln Glu His Ile Ser Pro Gln Ile Thr Asn Glu
            115                 120                 125

Val Ile Gly Pro Glu Leu Val His Val Ser Glu Lys Asn Leu Ser Glu
        130                 135                 140

Ile Glu Asn Val His Gly Phe Val Ser His Ser His Ile Ser Pro Ile
145                 150                 155                 160

Lys Pro Thr Glu Ala Val Leu Pro Ser Pro Pro Thr Val Pro Val Ile
                165                 170                 175
```

-continued

```
Pro Val Leu Pro Val Pro Ala Glu Asn Thr Val Ile Leu Pro Thr Ile
            180                 185                 190

Pro Gln Ala Asn Pro Pro Val Leu Val Asn Thr Asp Ser Leu Glu
            195                 200                 205

Thr Pro Thr Tyr Val Asn Gly Thr Asp Ala Asp Tyr Glu Tyr Glu
            210                 215                 220

Ile Thr Leu Glu Arg Gly Asn Ser Gly Leu Gly Phe Ser Ile Ala Gly
225                 230                 235                 240

Gly Thr Asp Asn Pro His Ile Gly Asp Asp Ser Ser Ile Phe Ile Thr
            245                 250                 255

Lys Ile Ile Thr Gly Gly Ala Ala Gln Asp Gly Arg Leu Arg Val
            260                 265                 270

Asn Asp Cys Ile Leu Gln Val Asn Glu Val Asp Val Arg Asp Val Thr
            275                 280                 285

His Ser Lys Ala Val Glu Ala Leu Lys Glu Ala Gly Ser Ile Val Arg
            290                 295                 300

Leu Tyr Val Lys Arg Arg Lys Pro Val Ser Glu Lys Ile Met Glu Ile
305                 310                 315                 320

Lys Leu Ile Lys Gly Pro Lys Gly Leu Gly Phe Ser Ile Ala Gly Gly
            325                 330                 335

Val Gly Asn Gln His Ile Pro Gly Asp Asn Ser Ile Tyr Val Thr Lys
            340                 345                 350

Ile Ile Glu Gly Gly Ala Ala His Lys Asp Gly Lys Leu Gln Ile Gly
            355                 360                 365

Asp Lys Leu Leu Ala Val Asn Asn Val Cys Leu Glu Glu Val Thr His
            370                 375                 380

Glu Glu Ala Val Thr Ala Leu Lys Asn Thr Ser Asp Phe Val Tyr Leu
385                 390                 395                 400

Lys Val Ala Lys Pro Thr Ser Met Tyr Met Asn Asp Gly Tyr Ala Pro
            405                 410                 415

Pro Asp Ile Thr Asn Ser Ser Gln Pro Val Asp Asn His Val Ser
            420                 425                 430

Pro Ser Ser Phe Leu Gly Gln Thr Pro Ala Ser Pro Ala Arg Tyr Ser
            435                 440                 445

Pro Val Ser Lys Ala Val Leu Gly Asp Asp Glu Ile Thr Arg Glu Pro
            450                 455                 460

Arg Lys Val Val Leu His Arg Gly Ser Thr Gly Leu Gly Phe Asn Ile
465                 470                 475                 480

Val Gly Gly Glu Asp Gly Glu Gly Ile Phe Ile Ser Phe Ile Leu Ala
            485                 490                 495

Gly Gly Pro Ala Asp Leu Ser Gly Glu Leu Arg Lys Gly Asp Arg Ile
            500                 505                 510

Ile Ser Val Asn Ser Val Asp Leu Arg Ala Ala Ser His Glu Gln Ala
            515                 520                 525

Ala Ala Ala Leu Lys Asn Ala Gly Gln Ala Val Thr Ile Val Ala Gln
            530                 535                 540

Tyr Arg Pro Glu Glu Tyr Ser Arg Phe Glu Ala Lys Ile His Asp Leu
545                 550                 555                 560

Arg Glu Gln Met Met Asn Ser Ser Ile Ser Ser Gly Ser Gly Ser Leu
            565                 570                 575

Arg Thr Ser Gln Lys Arg Ser Leu Tyr Val Arg Ala Leu Phe Asp Tyr
            580                 585                 590
```

| | | | | | | | | | | | |
|---|---|---|---|---|---|---|---|---|---|---|---|
|Asp|Lys|Thr|Lys|Asp|Ser|Gly|Leu|Pro|Ser|Gln|Gly|Leu|Asn|Phe|Lys|
| |595| | | |600| | | |605| | |

Phe Gly Asp Ile Leu His Val Ile Asn Ala Ser Asp Glu Trp Trp
610 615 620

Gln Ala Arg Gln Val Thr Pro Asp Gly Glu Ser Asp Glu Val Gly Val
625 630 635 640

Ile Pro Ser Lys Arg Val Glu Lys Glu Arg Ala Arg Leu Lys
645 650 655

Thr Val Lys Phe Asn Ser Lys Thr Arg Asp Lys Gly Glu Ile Pro Asp
660 665 670

Asp Met Gly Ser Lys Gly Leu Lys His Val Thr Ser Asn Ala Ser Asp
675 680 685

Ser Glu Ser Ser Tyr Arg Gly Gln Glu Glu Tyr Val Leu Ser Tyr Glu
690 695 700

Pro Val Asn Gln Gln Glu Val Asn Tyr Thr Arg Pro Val Ile Ile Leu
705 710 715 720

Gly Pro Met Lys Asp Arg Ile Asn Asp Asp Leu Ile Ser Glu Phe Pro
725 730 735

Asp Lys Phe Gly Ser Cys Val Pro His Thr Thr Arg Pro Lys Arg Asp
740 745 750

Tyr Glu Val Asp Gly Arg Asp Tyr His Phe Val Thr Ser Arg Glu Gln
755 760 765

Met Glu Lys Asp Ile Gln Glu His Lys Phe Ile Glu Ala Gly Gln Tyr
770 775 780

Asn Asn His Leu Tyr Gly Thr Ser Val Gln Ser Val Arg Glu Val Ala
785 790 795 800

Gly Lys Gly Lys His Cys Ile Leu Asp Val Ser Gly Asn Ala Ile Lys
805 810 815

Arg Leu Gln Ile Ala Gln Leu Tyr Pro Ile Ser Ile Phe Ile Lys Pro
820 825 830

Lys Ser Met Glu Asn Ile Met Glu Met Asn Lys Arg Leu Thr Glu Glu
835 840 845

Gln Ala Arg Lys Thr Phe Glu Arg Ala Met Lys Leu Glu Gln Glu Phe
850 855 860

Thr Glu His Phe Thr Ala Ile Val Gln Gly Asp Thr Leu Glu Asp Ile
865 870 875 880

Tyr Asn Gln Val Lys Gln Ile Ile Glu Glu Gln Ser Gly Ser Tyr Ile
885 890 895

Trp Val Pro Ala Lys Glu Lys Leu
900

<210> SEQ ID NO 3
<211> LENGTH: 3150
<212> TYPE: DNA
<213> ORGANISM: Mus musculus
<220> FEATURE:
<221> NAME/KEY: misc_feature
<223> OTHER INFORMATION: murine Dlg(discs large) gene

<400> SEQUENCE: 3

```
ggagaaaaat gccggtccgg aagcaagata cccagagagc attgcatctg ttggaagaat     60
atcgatcgaa actaagccaa actgaagaca gacaactcag aagttccata gagcgggtta    120
ttaacatatt tcagagcaac ctctttcagg ctttaataga tattcaagaa tttttatgaag   180 tgaccttact tgataatcca aaatgtgtgg atcattcaaa gcagtgtgaa ccagttcagc    240
```

```
ctgtgactac ttgggagatt gccagccttc caagcactgc cgtgacgtca gaaaccctgc    300
ccggcagcct tagccctcca gtagagaaat accggtatca ggatgaagag gtacttcctc    360
ctgagcatat ttctccacaa gtcacaaatg aggtgctagg tccagaactg gtccatgtct    420
cagagaagaa cctgtcagag attgagaatg tccatggatt tgtttctcat tctcatatct    480
caccaataaa gcccacagaa gctgttcctc cctcctctcc cattgtccct gtgaccctg     540 ccctgccagt ccctgctgag agtactgtcg tcctgccctc cgcaccacag gcaaatcctc    600
ctccagtgct ggtcaacaca gacagcttag agacaccaac ttatgttaat ggcactgatg    660
cagattatga atatgaggaa atcacacttg aaggggaaa ttcgggtctt ggtttcagca     720
ttgcaggagg tacagacaac ccacacattg gagatgactc aagtattttc atcaccaaaa    780
ttatcacagg cggacgggct gcccaggatg aagattgcg gtaaatgac tgtgtactga      840 gagtaaatga agcagacgtt cgtgatgtaa cccacagcaa agcagtggag gcattaaaag    900
aagctggatc tattgtgcga ttgtatgtga aaggcggaa gctagcatca gaaaaaatca     960
tggaaataaa gctcattaaa ggtcctaaag gtcttgggtt cagcattgct ggaggtattg    1020
gaaatcagca cattcctggt gataacagca tctatgtaac caaataatt gaaggaggtg     1080 cagcacacaa ggatggcaag cttcagattg gagataagct tctagcagtg aacagtgtgt    1140
gtttagaaga agttactcat gaagaagcag tgactgcctt aaagaataca tctgattttg    1200
tttatttgaa agtggcaaaa ccaacaagta tgtatataaa tgatggctat gcaccacctg    1260
acatcactaa ttcttcttct caatctgttg acaaccatgt cagcccgtcc tcctgcttgg    1320
gccagacgcc aacgtcacca gccaggtact cacccatttc taaagctgtg ctcggagatg    1380
acgagatcac tagggaacct agaaaagttg ttcttcatcg tggctcaaca ggacttggtt    1440
ttaacattgt ggcaggtgaa gatggagaag ggattttat ctccttcatc cttgctggcg     1500
gacctgctga tctaagtgga gagctcgaaa aaggagatcg catcatatcg gtgaacagtg    1560
ttgacctcag agctgcaagt cacgaacaag cagcagctgc actaaagaac gcaggccaag    1620
ccgtcaccat cgttgcgcaa tatcgacccg aagagtcacg tcgttttgaa gctaaaatcc    1680
atgacttacg ggagcagatg atgaatagca gagtcagttc agggtcaggg tctcctcgaa    1740
ccagccagaa gcgctccctc tatgtcagag ccctctttga ttatgacaag actaaggaca    1800
gcgggcttcc cagtcaagga ctgaacttcc gctttggaga catcctccat gtcatcaatg    1860
cttctgacga cgagtggtgg caagccaggc aggtcacccc agacggggag agtgacgaag    1920
tcggagtgat tcctagtaaa cgaagagctg agaagaagga acgagcccga ttaaaaacgg    1980
tcaaattcaa ttctaaaaca agaggagata aagggcagtc attcaatgac aagcgtaaaa    2040
agaacctctt ttcccgaaaa tttcccttct acaagaacaa ggaccagagt gaacaggaaa    2100
cgagtgatgc tgaccagcac gtaacttcta atgccagcga tagtgaaagt agttaccgtg    2160
gtcaagaaga atgtgtttta tcttatgagc cagtgaatca acaagaagtt aattataccc    2220
gaccagtcat catattagga cctatgaaag acagagtaaa tgatgactta atctcagaat    2280
ttcctgacaa atttggatcc tgtgtccctc atacaactag accgaagcgt gacatagagg    2340
tggatggacg agattatcat tttgtgactt caagggaacg agtggaaaag gatattcagg    2400
agcataagtt cattgaagcc ggccagtata acaaccatct gtatgggacg agcgtgcagt    2460
ccgtgcgagc agtggcagag aagggcaaac attgtatcct tgatgtgtct ggaaatgcca    2520
taaagaggtt gcagattgca cagctttatc caatatctat tttattaaaa cccaaatcca    2580
tggaaaatat catggaaatg aacaagcgcc taacagaaga gcaggccaga aaaacatttg    2640
```

-continued

```
agagagccat gaagctggag caggagttca ctgagcattt cacagctatt gtccagggag    2700
acacgctgga ggacatttac aaccaagtga aacagatcat cgaagaacag tctgggcctt    2760
acatctggga cctagcgaaa gaaaagctat gaagacggga gttgttcttt cttttttcca    2820
tggtctcatc tcttgccctg ttgtggagtc tgtcttcggt gtcctccacg ctgacacaga    2880 tccctcctc atggtcggca gttgtgcccg ttttttgaca tctgtgtccc ttcatgttgc     2940
atcatctgta ctattctgtg ttactcttgg tttctggcca cttttcggaa tgaagatgaa    3000
tggcctgacc agctatctag ggtttgggga gatgtaaaat tgtaaaattc cttaatgttt    3060
aagggaaagt taactttaag agattttcag aaaagcttta tatacactct tttccaatct    3120
cagtacaaat gaaaaaaaaa aaaaaaaaa                                      3150
```

<210> SEQ ID NO 4
<211> LENGTH: 927
<212> TYPE: PRT
<213> ORGANISM: Mus musculus

<400> SEQUENCE: 4

```
Met Pro Val Arg Lys Gln Asp Thr Gln Arg Ala Leu His Leu Leu Glu
1               5                   10                  15

Glu Tyr Arg Ser Lys Leu Ser Gln Thr Glu Asp Arg Gln Leu Arg Ser
            20                  25                  30

Ser Ile Glu Arg Val Ile Asn Ile Phe Gln Ser Asn Leu Phe Gln Ala
        35                  40                  45

Leu Ile Asp Ile Gln Glu Phe Tyr Glu Val Thr Leu Leu Asp Asn Pro
    50                  55                  60

Lys Cys Val Asp His Ser Lys Gln Cys Glu Pro Val Gln Pro Val Thr
65                  70                  75                  80

Thr Trp Glu Ile Ala Ser Leu Pro Ser Thr Ala Val Thr Ser Glu Thr
                85                  90                  95

Leu Pro Gly Ser Leu Ser Pro Val Glu Lys Tyr Arg Tyr Gln Asp
            100                 105                 110

Glu Glu Val Leu Pro Pro Glu His Ile Ser Pro Gln Val Thr Asn Glu
        115                 120                 125

Val Leu Gly Pro Glu Leu Val His Val Ser Glu Lys Asn Leu Ser Glu
    130                 135                 140

Ile Glu Asn Val His Gly Phe Val Ser His Ser His Ile Ser Pro Ile
145                 150                 155                 160

Lys Pro Thr Glu Ala Val Pro Pro Ser Ser Pro Ile Val Pro Val Thr
                165                 170                 175

Pro Ala Leu Pro Val Pro Ala Glu Ser Thr Val Leu Pro Ser Ala
            180                 185                 190

Pro Gln Ala Asn Pro Pro Val Leu Val Asn Thr Asp Ser Leu Glu
        195                 200                 205

Thr Pro Thr Tyr Val Asn Gly Thr Asp Ala Asp Tyr Glu Tyr Glu Glu
    210                 215                 220

Ile Thr Leu Glu Arg Gly Asn Ser Gly Leu Gly Phe Ser Ile Ala Gly
225                 230                 235                 240

Gly Thr Asp Asn Pro His Ile Gly Asp Ser Ser Ile Phe Ile Thr
                245                 250                 255

Lys Ile Ile Thr Gly Gly Arg Ala Ala Gln Asp Gly Arg Leu Arg Val
            260                 265                 270

Asn Asp Cys Val Leu Arg Val Asn Glu Ala Asp Val Arg Asp Val Thr
```

-continued

```
                275                 280                 285
His Ser Lys Ala Val Glu Ala Leu Lys Glu Ala Gly Ser Ile Val Arg
    290                 295                 300

Leu Tyr Val Lys Arg Arg Lys Leu Ala Ser Glu Lys Ile Met Glu Ile
305                 310                 315                 320

Lys Leu Ile Lys Gly Pro Lys Gly Leu Gly Phe Ser Ile Ala Gly Gly
                325                 330                 335

Ile Gly Asn Gln His Ile Pro Gly Asp Asn Ser Ile Tyr Val Thr Lys
            340                 345                 350

Ile Ile Glu Gly Gly Ala Ala His Lys Asp Gly Lys Leu Gln Ile Gly
        355                 360                 365

Asp Lys Leu Leu Ala Val Asn Ser Val Cys Leu Glu Glu Val Thr His
    370                 375                 380

Glu Glu Ala Val Thr Ala Leu Lys Asn Thr Ser Asp Phe Val Tyr Leu
385                 390                 395                 400

Lys Val Ala Lys Pro Thr Ser Met Tyr Ile Asn Asp Gly Tyr Ala Pro
                405                 410                 415

Pro Asp Ile Thr Asn Ser Ser Gln Ser Val Asp Asn His Val Ser
            420                 425                 430

Pro Ser Ser Cys Leu Gly Gln Thr Pro Thr Ser Pro Ala Arg Tyr Ser
        435                 440                 445

Pro Ile Ser Lys Ala Val Leu Gly Asp Asp Glu Ile Thr Arg Glu Pro
    450                 455                 460

Arg Lys Val Val Leu His Arg Gly Ser Thr Gly Leu Gly Phe Asn Ile
465                 470                 475                 480

Val Ala Gly Glu Asp Gly Glu Gly Ile Phe Ile Ser Phe Ile Leu Ala
                485                 490                 495

Gly Gly Pro Ala Asp Leu Ser Gly Glu Leu Arg Lys Gly Asp Arg Ile
            500                 505                 510

Ile Ser Val Asn Ser Val Asp Leu Arg Ala Ala Ser His Glu Gln Ala
        515                 520                 525

Ala Ala Ala Leu Lys Asn Ala Gly Gln Ala Val Thr Ile Val Ala Gln
    530                 535                 540

Tyr Arg Pro Glu Glu Ser Arg Arg Phe Glu Ala Lys Ile His Asp Leu
545                 550                 555                 560

Arg Glu Gln Met Met Asn Ser Arg Val Ser Ser Gly Ser Gly Ser Pro
                565                 570                 575

Arg Thr Ser Gln Lys Arg Ser Leu Tyr Val Arg Ala Leu Phe Asp Tyr
            580                 585                 590

Asp Lys Thr Lys Asp Ser Gly Leu Pro Ser Gln Gly Leu Asn Phe Arg
        595                 600                 605

Phe Gly Asp Ile Leu His Val Ile Asn Ala Ser Asp Glu Trp Trp
    610                 615                 620

Gln Ala Arg Gln Val Thr Pro Asp Gly Glu Ser Asp Glu Val Gly Val
625                 630                 635                 640

Ile Pro Ser Lys Arg Arg Ala Glu Lys Lys Glu Arg Ala Arg Leu Lys
                645                 650                 655

Thr Val Lys Phe Asn Ser Lys Thr Arg Gly Asp Lys Gly Gln Ser Phe
            660                 665                 670

Asn Asp Lys Arg Lys Lys Asn Leu Phe Ser Arg Lys Phe Pro Phe Tyr
        675                 680                 685

Lys Asn Lys Asp Gln Ser Glu Gln Glu Thr Ser Asp Ala Asp Gln His
    690                 695                 700
```

-continued

```
Val Thr Ser Asn Ala Ser Asp Ser Glu Ser Ser Tyr Arg Gly Gln Glu
705                 710                 715                 720

Glu Cys Val Leu Ser Tyr Glu Pro Val Asn Gln Gln Glu Val Asn Tyr
            725                 730                 735

Thr Arg Pro Val Ile Ile Leu Gly Pro Met Lys Asp Arg Val Asn Asp
        740                 745                 750

Asp Leu Ile Ser Glu Phe Pro Asp Lys Phe Gly Ser Cys Val Pro His
    755                 760                 765

Thr Thr Arg Pro Lys Arg Asp Ile Glu Val Asp Gly Arg Asp Tyr His
770                 775                 780

Phe Val Thr Ser Arg Glu Arg Val Lys Asp Ile Gln Glu His Lys
785                 790                 795                 800

Phe Ile Glu Ala Gly Gln Tyr Asn Asn His Leu Tyr Gly Thr Ser Val
            805                 810                 815

Gln Ser Val Arg Ala Val Ala Glu Lys Gly Lys His Cys Ile Leu Asp
        820                 825                 830

Val Ser Gly Asn Ala Ile Lys Arg Leu Gln Ile Ala Gln Leu Tyr Pro
    835                 840                 845

Ile Ser Ile Phe Ile Lys Pro Lys Ser Met Glu Asn Ile Met Glu Met
850                 855                 860

Asn Lys Arg Leu Thr Glu Glu Gln Ala Arg Lys Thr Phe Glu Arg Ala
865                 870                 875                 880

Met Lys Leu Glu Gln Glu Phe Thr Glu His Phe Thr Ala Ile Val Gln
            885                 890                 895

Gly Asp Thr Leu Glu Asp Ile Tyr Asn Gln Val Lys Gln Ile Ile Glu
        900                 905                 910

Glu Gln Ser Gly Pro Tyr Ile Trp Val Leu Ala Lys Glu Lys Leu
    915                 920                 925

<210> SEQ ID NO 5
<211> LENGTH: 20
<212> TYPE: DNA
<213> ORGANISM: Artificial
<220> FEATURE:
<223> OTHER INFORMATION: Designed polynucleotide for use as a primer

<400> SEQUENCE: 5
atgccggtcc ggaagcaaga                                               20

<210> SEQ ID NO 6
<211> LENGTH: 20
<212> TYPE: DNA
<213> ORGANISM: Artificial
<220> FEATURE:
<223> OTHER INFORMATION: Designed polynucleotide for use as a primer

<400> SEQUENCE: 6
tcttcatcct gatacctgta                                               20

<210> SEQ ID NO 7
<211> LENGTH: 30
<212> TYPE: DNA
<213> ORGANISM: Artificial
<220> FEATURE:
<223> OTHER INFORMATION: Designed polynucleotide for use as a primer

<400> SEQUENCE: 7
gctgtcagtc cacagctaac acaggctact                                    30
```

<210> SEQ ID NO 8
<211> LENGTH: 30
<212> TYPE: DNA
<213> ORGANISM: Artificial
<220> FEATURE:
<223> OTHER INFORMATION: Designed polynucleotide for use as a primer

<400> SEQUENCE: 8
tgtcctaagt taaggaccat ctagagagcc                            30

<210> SEQ ID NO 9
<211> LENGTH: 30
<212> TYPE: DNA
<213> ORGANISM: Artificial
<220> FEATURE:
<223> OTHER INFORMATION: Designed polynucleotide for use as a primer

<400> SEQUENCE: 9
tcgtgcttta cggtatcgcc gctcccgatt                            30

<210> SEQ ID NO 10
<211> LENGTH: 5229
<212> TYPE: DNA
<213> ORGANISM: Mus musculus
<220> FEATURE:
<221> NAME/KEY: misc_feature
<223> OTHER INFORMATION: H2-kk gene

<400> SEQUENCE: 10
gaattcgata tcactagtac gcgtcgacga gctcggatcc cgggaagctt cgatccagac      60
atgataagat acattgatga gtttggacaa accacaacta gaatgcagtg aaaaaaatgc     120
tttatttgtg aaatttgtga tgctattgct ttatttgtaa ccattataag ctgcaataaa     180
caagttaaca acaacaattg cattcatttt atgtttcagg ttcaggggga ggtgtgggag     240
gttttttaaa gcaagtaaaa cctctacaaa tgtggtatgg ctgattatga tccggctgcc     300
tcgcgcgttt cggtgatgac ggtgaaaacc tctgacacat gcagctcccg agacggtca      360 cagcttgtct gtaagcggat gccgggagca gacaagcccg tcagggcgcg tcagcgggtg     420
ttggcgggtg tcgggcgcag ccatgacccc tgcattaat gaatcggcca acgcgcgggg     480
agaggcggtt tgcgtattgg gcgctcttcc gcttcctcgc tcactgactc gctgcgctcg     540
gtcgttcggc tgcggcgagc ggtatcagct cactcaaagg cggtaatacg ttatccaca      600 gaatcagggg ataacgcagg aaagaacatg tgagcaaaag gccagcaaaa ggccaggaac     660
cgtaaaaagg ccgcgttgct ggcgtttttc cataggctcc gcccccctga cgagcatcac     720
aaaaatcgac gctcaagtca gaggtggcga acccgacag gactataaag ataccaggcg      780
tttccccctg gaagctccct cgtgcgctct cctgttccga ccctgccgct taccggatac     840
ctgtccgcct ttctcccttc gggaagcgtg gcgctttctc atagctcacg ctgtaggtat     900
ctcagttcgg tgtaggtcgt tcgctccaag ctgggctgtg tgcacgaacc cccgttcag     960 cccgaccgct gcgccttatc cggtaactat cgtcttgagt ccaacccggt aagacacgac    1020
ttatcgccac tggcagcagc cactggtaac aggattagca gagcgaggta tgtaggcggt    1080
gctacagagt tcttgaagtg gtggcctaac tacggctaca ctagaagaac agtatttggt    1140
atctgcgctc tgctgaagcc agttaccttc ggaaaaagag ttggtagctc ttgatccggc    1200
aaacaaacca ccgctggtag cggtggtttt tttgtttgca agcagcagat tacgcgcaga    1260
aaaaaaggat ctcaagaaga tcctttgatc ttttctacgg ggtctgacgc tcagtggaac    1320

```
gaaaactcac gttaagggat tttgctcatg agacaataac cctgataaat gcttcaataa   1380
tattgaaaaa ggaagagtat gagtattcaa catttccgtg tcgcccttat tccctttttt   1440
gcggcatttt gccttcctgt ttttgctcac ccagaaacgc tggtgaaagt aaaagatgct   1500
gaagatcagt tgggtgcacg agtgggttac atcgaactgg atctcaacag cggtaagatc   1560
cttgagagtt ttcgccccga agaacgtttt ccaatgatga gcacttttaa agttctgcta   1620
tgtggcgcgg tattatcccg tattgacgcc gggcaagagc aactcggtcg ccgcatacac   1680
tattctcaga atgacttggt tgagtactca ccagtcacag aaaagcatct tacgatggc    1740 atgacagtaa gagaattatg cagtgctgcc ataaccatga gtgataacac tgcggccaac   1800
ttacttctga caacgatcgg aggaccgaag gagctaaccg cttttttgca caacatgggg   1860
gatcatgtaa ctcgccttga tcgttgggaa ccggagctga atgaagccat accaaacgac   1920
gagcgtgaca ccacgatgcc tgtagcaatg gcaacaacgt tgcgcaaact attaactggc   1980
gaactactta ctctagcttc ccggcaacaa ttaatagact ggatggaggc ggataaagtt   2040
gcaggaccac ttctgcgctc ggcccttccg gctggctggt ttattgctga taaatctgga   2100
gccggtgagc gtgggtctcg cggtatcatt gcagcactgg ggccagatgg taagccctcc   2160
cgtatcgtag ttatctacac gacggggagt caggcaacta tggatgaacg aaatagacag   2220
atcgctgaga taggtgcctc actgattaag cattggtaac tgtcagacca agtttactca   2280
tatatacttt agattgattt aaaacttcat ttttaattta aaaggatcta ggtgaagatc   2340
cctagcttat cggccaattc ggatctttta ttggatctct agagaaatgt tctggcacct   2400
gcacttgcac tggggacagc ctattttgct agtttgtttt gtttcgtttt gttttgatgg   2460
agagcgtatg ttcggtaccc cacacaaaaa accaacacac agatctaatg aaaataaaga   2520
tcttttattg gatcggggat ctaccctcct tttccacctg tgtttctcct tctcatcttc   2580
atcacaaaag ccaccacagc tccagtgact attgcagctc caaggacaac cagaacagca   2640
atgattaccg tgttggagac agtggatgga ggaggctccc atctcagggt gaggggctca   2700
ggcagcccct gatggtacac atggcatgtg taatactgct ccttcccaag aggcaccacc   2760
acagatgccc acttctggaa ggttccatcc cctgcaggcc tggtctccac aagctccatg   2820
tcctgggtca gctcctcccc attcaactgc caggtcaggg tgatgtcagc agggtagaag   2880
cccagggccc agcacctcag ggtgacttta tcttcaggtc tgctgtgacg ggtcacatgg   2940
gcctttgggg aatctgtgcg cggcagcgtc gcgttcccga gctgcaggta tctgcggagc   3000
cactccacgc acgtgccctc caggtaggcc cggtctctct ctgcatcacc agcctgctcc   3060
cacttgtgtt tggtgatcag cgccgccatg tcggccgccg tccacgtttt caggtcttcg   3120
ttcagggcga tgtaatcgca gccgtcgtat gcgtactgct cgtacccgcg gaggaggcgc   3180
cagtccgacc ccacctcaca gccgtacatc cgttggaacg tgtgagagcc gcccgcgctc   3240
tggttgtagt agcgcagcgc ggtcctcagg ttcactcgga aaatctgctc attgcccttg   3300
gcgatctgcg tgttccgctc ccaatactcg ggctccacct gctccatcca ccgcacccgc   3360
ggctcatacc tcggattctc cgcgtcgctg tcgaagcgca cgaactgcgt gtcgtccacg   3420
tagccgacag agatgaaccg gggcttcccg aggccgggcc gggacacggc ggtgtggaaa   3480
tacctcagcg aatgtgggcc cgcgcgggtc tgagtcgggg ccagggcggc cgccaacagc   3540
```

-continued

```
aggagcagca tgcagggtgc catcgcaccg gtcggcgatt cgagacttct gagttccgcg  3600
ggctgcgtgg actttatagc cagcgtccgc ggcgacactg attggttctt ggtgatcgcg  3660
ccacccaatg ggggtaagag ctgactgcgc gtcaacagtg tccggacaga aggacctgac  3720
ccaggttagg agcagaagtg aaactgtgga gatggggaat ccccagccct gggcttcccc  3780
accoctgacc tcaccgcctg gcaactaaga ctttgcctga accctgtgct gtcgtctccg  3840
agttctgatc cagaaactct caaaacacca ggagagaccc gcaggccaga ctctctgtgt  3900
cctctcttcc actcttcctc ttccttcttc tcttcagaag tcagaccctg gagtcttcta  3960
gaagaaaagc ctcttccggg aatacaatgg tgacacaagc gcttagggat gcagtggaga  4020
gaggcttttc cttaaagtcg aggctctggg ctgcaagccc cacacggacc ccacagagac  4080
caggctctgt tcacctgcaa tgggtggctc acactgccaa gcctgagtgc aggactcatc  4140
tgttaagtgt agacttcgcc tctcccctca ggatctgtct tctcagccct gtgctgagac  4200
acagattcct tgtgttaatt cctagatgaa gagtctgtgg ctgcaggtgt gtgtgtgtgt  4260
gtgtgtgtgt gtgtgtgtat ttgaaacaag gatcttcatt ctgagtcctg agtttgtctc  4320
tgtggacctg ggacattgtt tcagcacagg agacccccctt gtccactgaa gagagacccc  4380
tgtgcagacc acagacagca gggcactgat cgctgtctcc actggacttc tctgtgtctg  4440
cacttccatg gtgcagttgc tttagtgact taatcacagt aggagaggaa ctgtcaccaa  4500
ctataacaca gaataaggat gatagtgtgg tagaagttat gtaatttctg accctctccc  4560
tccctccctg accttcactc acacttatga gctgatgagg tgagggacat gaatgtcaca  4620
gctgtgtggg acactggttc tgataaccta gttggcccca gagttcctca ggggaattgg  4680
ccgatgataa gctgtcaaac atgagaattg gtcgatcgac caattcttga agacgaaagg  4740
gcctcgtgat acgcctattt ttataggtta atgtcatggg ccgataagct agcttggctg  4800
tggaatgtgt gtcagttagg gtgtggaaag tccccaggct ccccagcagg cagaagtatg  4860
caaagcatgc atctcaatta gtcagcaacc aggtgtggaa agtccccagg ctccccagca  4920
ggcagaagta tgcaaagcat gcatctcaat tagtcagcaa ccatagtccc gccctaact  4980
ccgcccatcc cgcccctaac tccgcccagt tccgcccatt ctccgcccca tggctgacta  5040
attttttta tttatgcaga ggccgaggcc gcctcggcct ctgagctatt ccagaagtag  5100
tgaggaggct tttttggagg cctaggcttt tgcaaaaagc tcctcgagga actgaaaaac  5160
cagaaagtta actggtaagt ttagtctttt tgtcttttat ttcaggtccc ggatcggaat  5220
tgcggccgc                                                           5229
```